United States Patent
Zhang et al.

(10) Patent No.: US 11,572,421 B2
(45) Date of Patent: Feb. 7, 2023

(54) LOW MOLECULAR WEIGHT CHONDROITIN SULFATE, COMPOSITION, PREPARATION METHOD AND USE THEREOF

(71) Applicant: NANJING HANXIN PHARMACEUTICAL TECHNOLOGY CO., LTD., Jiangsu (CN)

(72) Inventors: Haoning Zhang, Jiangsu (CN); Song Chen, Jiangsu (CN); Bo Jin, Jiangsu (CN); Yonggang Xu, Jiangsu (CN); Chuangen Tang, Jiangsu (CN)

(73) Assignee: Nanjing Hanxin Pharmaceutical Technology Co., Ltd., Jiangsu (CN)

( * ) Notice: Subject to any disclaimer, the term of this patent is extended or adjusted under 35 U.S.C. 154(b) by 0 days.

(21) Appl. No.: 17/335,837

(22) Filed: Jun. 1, 2021

(65) Prior Publication Data

US 2021/0340283 A1 Nov. 4, 2021

Related U.S. Application Data

(63) Continuation of application No. PCT/CN2020/126003, filed on Nov. 2, 2020.

(30) Foreign Application Priority Data

| Nov. 1, 2019 | (WO) | PCT/CN2019/115120 |
| Mar. 13, 2020 | (WO) | PCT/CN2020/079335 |
| Sep. 30, 2020 | (CN) | 202011070381.2 |

(51) Int. Cl.

| *C08B 37/00* | (2006.01) |
| *A61P 19/02* | (2006.01) |
| *A61P 19/10* | (2006.01) |
| *C12P 19/04* | (2006.01) |

(52) U.S. Cl.
CPC .......... *C08B 37/0069* (2013.01); *A61P 19/02* (2018.01); *A61P 19/10* (2018.01); *C12P 19/04* (2013.01); *C12Y 402/0202* (2013.01)

(58) Field of Classification Search
CPC ...... C08B 37/0069; A61P 19/02; C12P 19/04; C12Y 402/0202
See application file for complete search history.

(56) References Cited

U.S. PATENT DOCUMENTS

| 3,405,120 A | 10/1968 | Kawano et al. | |
| 5,344,451 A * | 9/1994 | Dayton | A61L 27/20 623/7 |
| 2015/0152198 A1 | 6/2015 | Miraglia et al. | |

FOREIGN PATENT DOCUMENTS

| CN | 1513471 A | 7/2004 |
| CN | 101057862 A | 10/2007 |
| CN | 101658482 A | 3/2010 |
| CN | 102228466 A | 11/2011 |
| CN | 102676613 A | 9/2012 |
| CN | 103602711 A | 2/2014 |
| CN | 103602771 A | 2/2014 |
| CN | 103623006 A | 3/2014 |
| CN | 104411363 A | 3/2015 |
| CN | 108070627 A | 5/2018 |
| CN | 109913437 A | 6/2019 |
| JP | 2000273102 A | 10/2000 |
| JP | 3278629 B2 | 4/2002 |
| KR | 20060100894 A | 9/2006 |

OTHER PUBLICATIONS

U.S. Appl. No. 17/335,837 CN102676613B MT (Year: 2013).*
U.S. Appl. No. 17/335,837 CN103602711B MT (Year: 2016).*
U.S. Appl. No. 17/335,837 CN108979627A MT (Year: 2018).*
Zhang et al., "Chondroitin Sulfate Oligosaccharides Prepared by Chondroitinase and its Antioxidant Activities," Science and Technology Food Industry, Aug. 2017, 38(13):48-52 (7 pages with English Abstract).
PCT International Search Report for PCT Application No. PCT/CN2020/079335 dated Dec. 14, 2020 (4 pages).

* cited by examiner

*Primary Examiner* — Leigh C Maier
*Assistant Examiner* — Everett White
(74) *Attorney, Agent, or Firm* — Merchant & Gould P.C.

(57) ABSTRACT

The invention relates to a low molecular weight sulfate chondroitin and a preparation method thereof. A low molecular weight chondroitin sulfate with the average molecular weight of less than 1000 Dalton can be obtained by a production process of chondroitin sulfate lyase degradation, deproteinization, filtration and sterilization and drying using macromolecular sulfate chondroitin as a raw material. The low molecular weight Chondroitin sulfate has a narrow molecular weight distribution range, the ratio of chondroitin sulfate disaccharide is 43~60% and the ratio of chondroitin sulfate tetrasaccharide is 30~45%, the sum of chondroitin sulfate disaccharide and chondroitin sulfate tetrasaccharide is more than 87%, the total oligosaccharide content of low molecular weight chondroitin sulfate is more than 97% and the protein content is less than 0.5%; Compared with the general market macromolecule chondroitin sulfate, the product has more remarkable repair effect at the concentration of 50~100 μg/mL on chondrocytes damaged by 1 mM hydrogen peroxide, with strong repair ability and repair rate of 14%~23%. The low molecular weight chondroitin sulfate can be used to treat joint injury and is an important raw material for medical products, health care products, cosmetics and food.

22 Claims, 22 Drawing Sheets

Result:

| # | Retention time min | Area mAu*min | Height mAu | Relative area % |
|---|---|---|---|---|
| 1 | 5.879 | 63.802 | 273.412 | 9.51 |
| 2 | 8.632 | 227.093 | 683.311 | 33.83 |
| 3 | 8.966 | 34.008 | 161.882 | 5.07 |
| 4 | 9.846 | 316.031 | 1206.905 | 47.08 |
| 5 | 10.786 | 13.644 | 57.738 | 2.03 |
| 6 | 12.506 | 16.647 | 40.171 | 2.48 |
|  | Total | 671.226 | 2423.420 | 100.00 |

Result:

| # | Retention time min | Area mAu*min | Height mAu | Relative area % |
|---|---|---|---|---|
| 1 | 5.878 | 62.295 | 266.655 | 9.50 |
| 2 | 8.625 | 222.305 | 674.104 | 33.90 |
| 3 | 8.958 | 33.314 | 158.498 | 5.08 |
| 4 | 9.838 | 307.233 | 1181.773 | 46.86 |
| 5 | 10.785 | 13.949 | 60.097 | 2.13 |
| 6 | 12.505 | 16.585 | 39.357 | 2.53 |
| | Total | 655.680 | 2380.490 | 100.00 |

| # | Retention time min | Area mAu*min | Height mAu | Relative area % |
|---|---|---|---|---|
| 1 | 5.879 | 66.217 | 298.224 | 8.62 |
| 2 | 8.632 | 236.598 | 726.700 | 30.79 |
| 3 | 8.966 | 33.857 | 172.479 | 4.41 |
| 4 | 9.872 | 403.340 | 1444.148 | 52.49 |
| 5 | 10.786 | 15.517 | 79.385 | 2.02 |
| 6 | 12.512 | 12.931 | 35.649 | 1.68 |
|   | Total | 768.458 | 2756.585 | 100.00 |

Result:

| # | Retention time min | Area mAu*min | Height mAu | Relative area % |
|---|---|---|---|---|
| 1 | 5.876 | 65.852 | 297.184 | 8.50 |
| 2 | 8.636 | 237.083 | 728.466 | 30.59 |
| 3 | 8.963 | 34.369 | 174.174 | 4.43 |
| 4 | 9.870 | 408.349 | 1457.432 | 52.69 |
| 5 | 10.783 | 16.555 | 84.899 | 2.14 |
| 6 | 12.510 | 12.780 | 35.923 | 1.65 |
|  | Total | 774.988 | 2778.079 | 100.00 |

| # | Retention time min | Area mAu*min | Height mAu | Relative area % |
|---|---|---|---|---|
| 1 | 9.265 | 363952 | 18001 | 2.28 |
| 2 | 10.070 | 10495949 | 589972 | 65.79 |
| 3 | 10.937 | 5093998 | 171236 | 31.93 |
|   | Total | 15953899 |   |   |

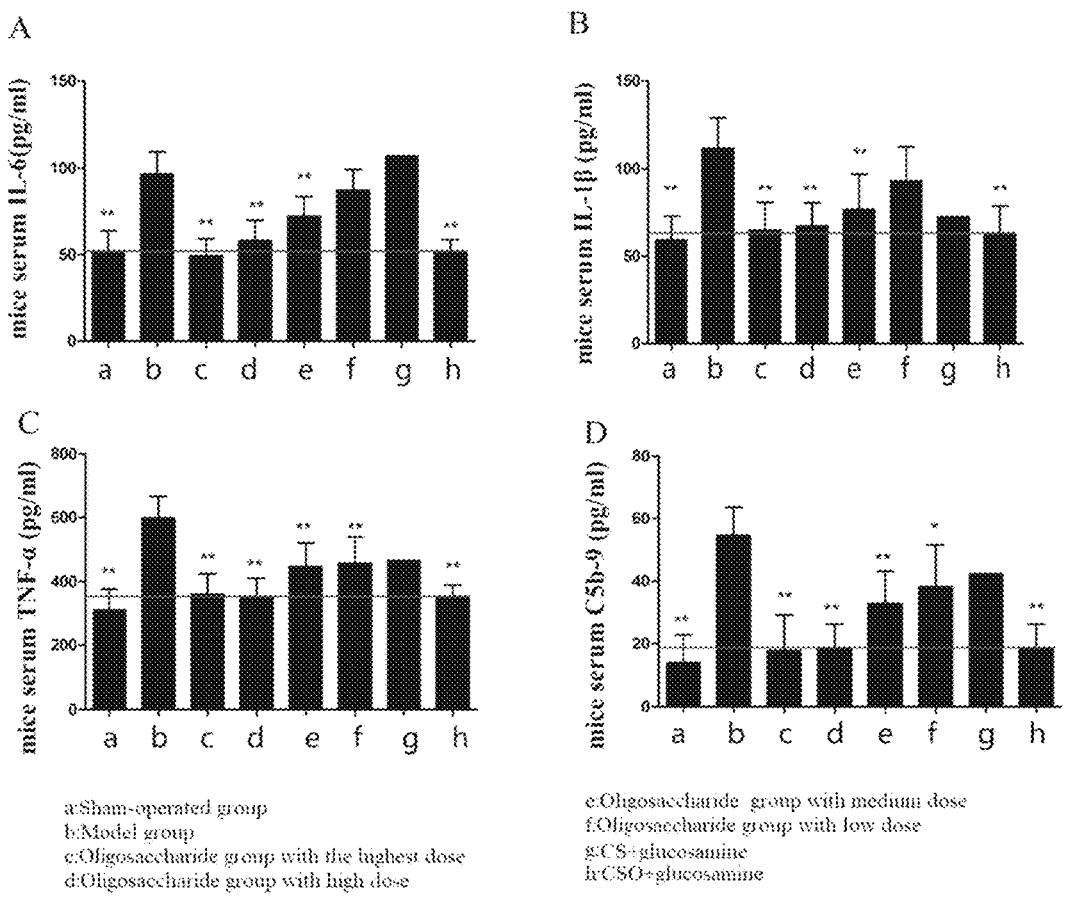
Fig. 10A Effects of different dose groups on serum IL-6(A), IL-1β (B), TNF-α(C) and C5b-9 (D) concentrations in mice
Highest dose group: 60 mg/kg
High dose group: 30 mg/kg
Medium dose group: 15 mg/kg
Low dose group: 7.5 mg/kg
CSO + glucosamine: CSO:15 mg/kg; glucosamine 75 mg/kg
CS+ glucosamine: CS:80 mg/kg; glucosamine 400 mg/kg

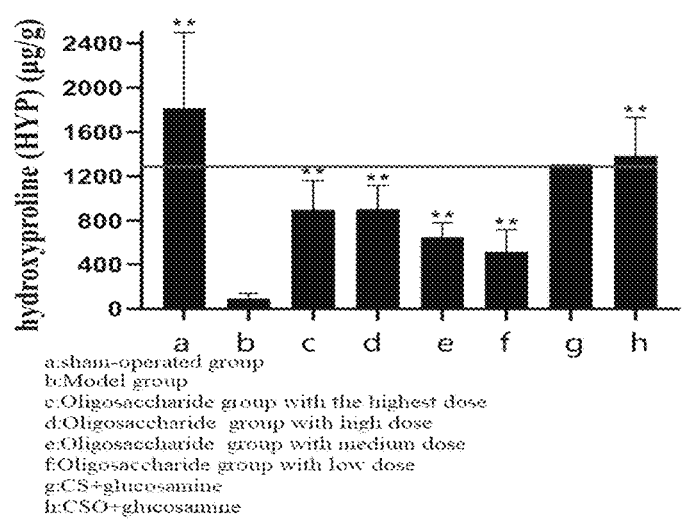
Fig. 10B Assay of hydroxyproline (HYP) level in femur of mice

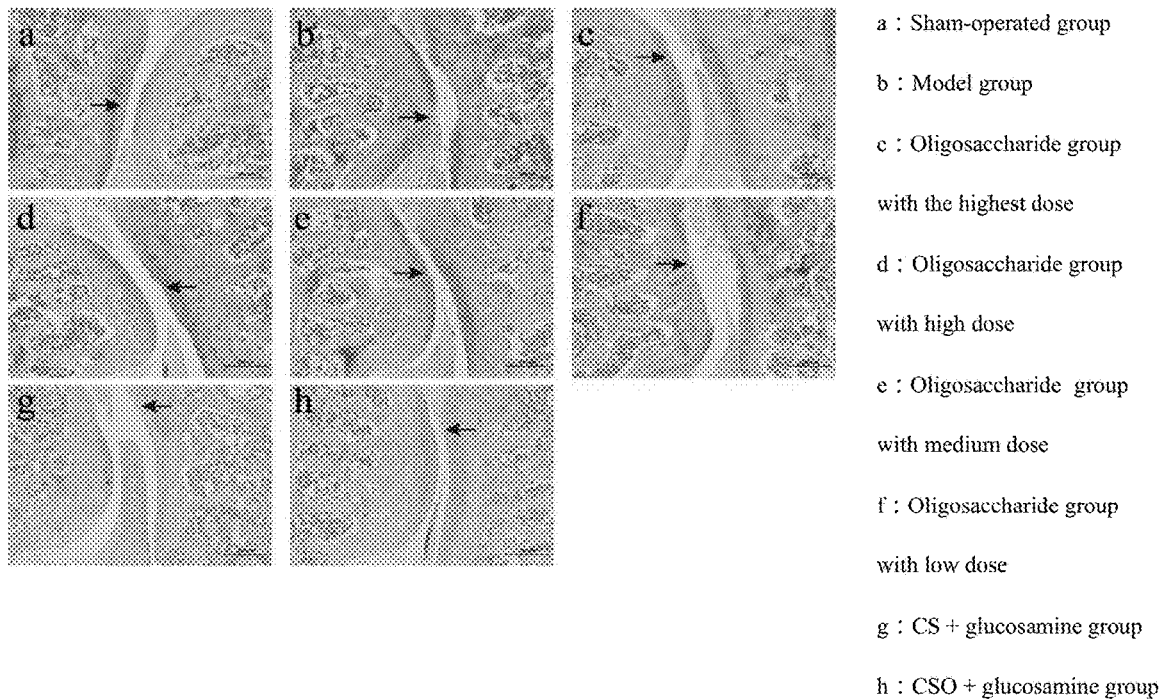

Fig.10C Mouse knee joint sanguine solid green staining (×100)

a : Sham-operated group
b : Model group
c : Oligosaccharide group with the highest dose
d : Oligosaccharide group with high dose
e : Oligosaccharide group with medium dose
f : Oligosaccharide group with low dose
g : CS + glucosamine group
h : CSO + glucosamine group

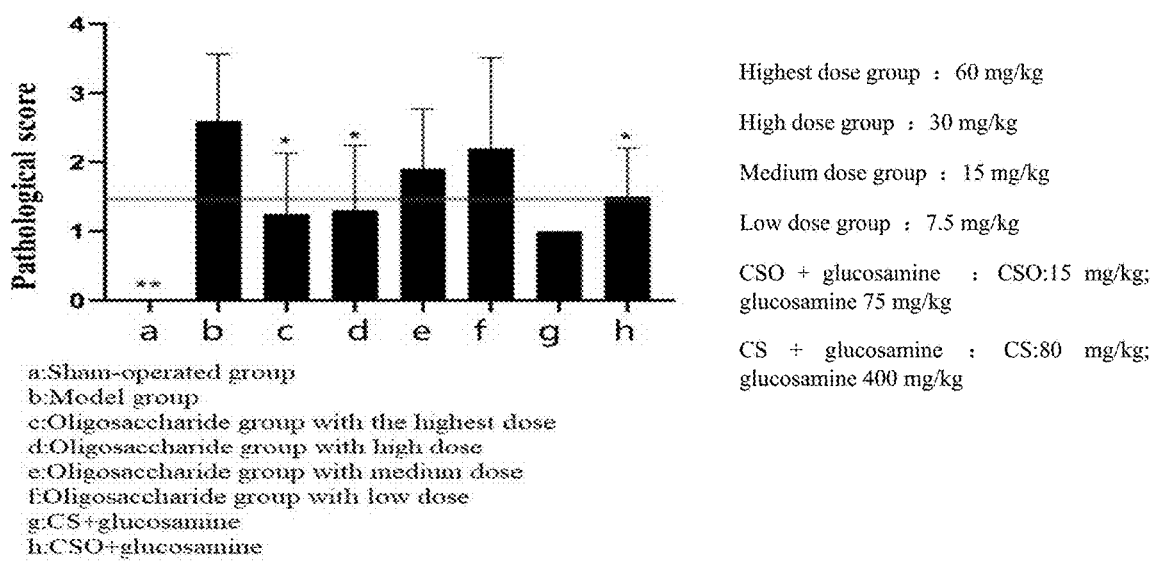

Fig.10D Pathological score upon safranin O-fast green staining in mouse knee joint a: Sham-operated group
b: Model group
c: Oligosaccharide group with the highest dose
d: Oligosaccharide group with high dose
e: Oligosaccharide group with medium dose
f: Oligosaccharide group with low dose
g: CS+glucosamine
h: CSO+glucosamine Highest dose group : 60 mg/kg
High dose group : 30 mg/kg
Medium dose group : 15 mg/kg
Low dose group : 7.5 mg/kg
CSO + glucosamine : CSO:15 mg/kg; glucosamine 75 mg/kg
CS + glucosamine : CS:80 mg/kg; glucosamine 400 mg/kg

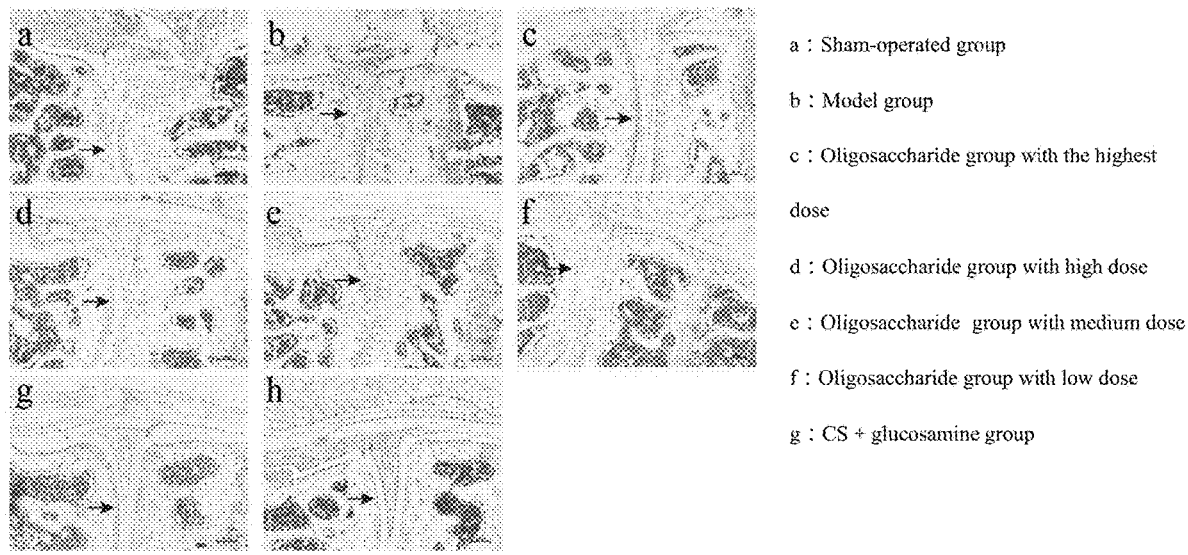
Fig.10E  Immunohistochemical staining in mouse knee C5b-9 (×100)
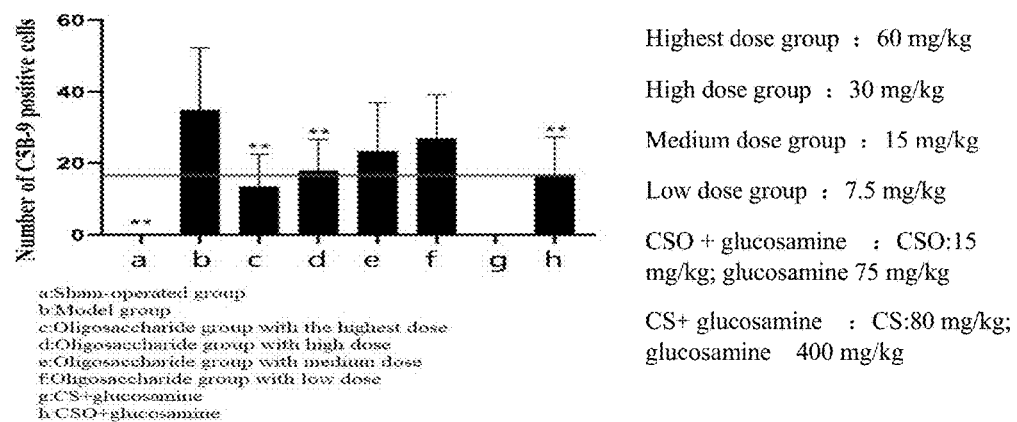
Fig.10F  Number of C5b-9 positive cells in mouse knee joint

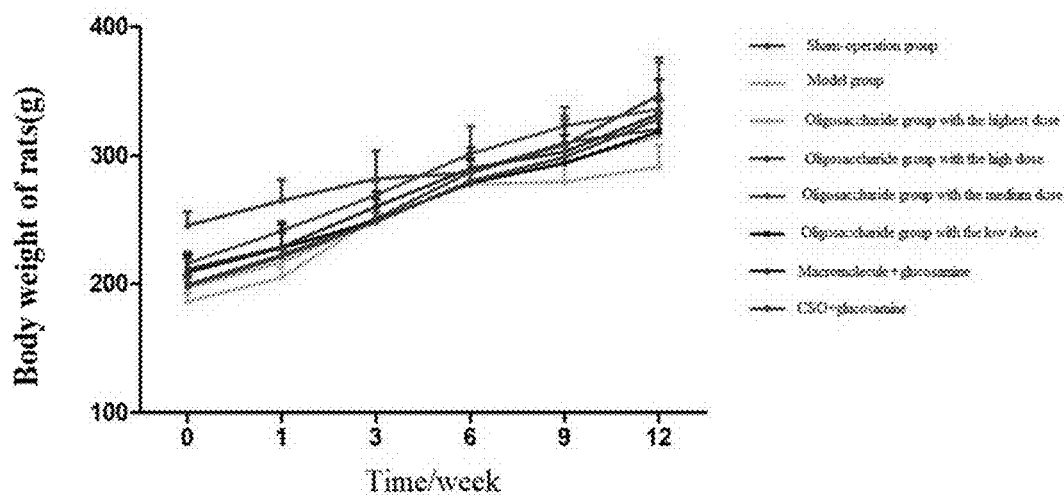
Fig.11A  Body weight changes in rats
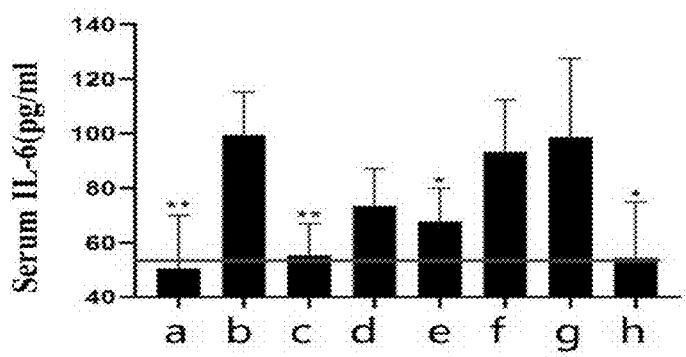
a:Sham-operated group
b:Model group
c:Oligosaccharide group with the highest dose
d:Oligosaccharide group with high dose
e:Oligosaccharide group with medium dose
f:Oligosaccharide group with low dose
g:CS+glucosamine
h:CSO+glucosamine
Fig.11B Serum IL-6 in rats

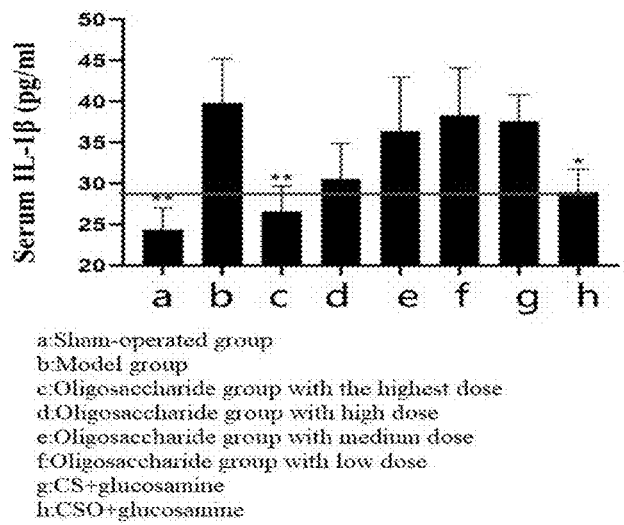
Fig.11C Serum IL-1β in rats
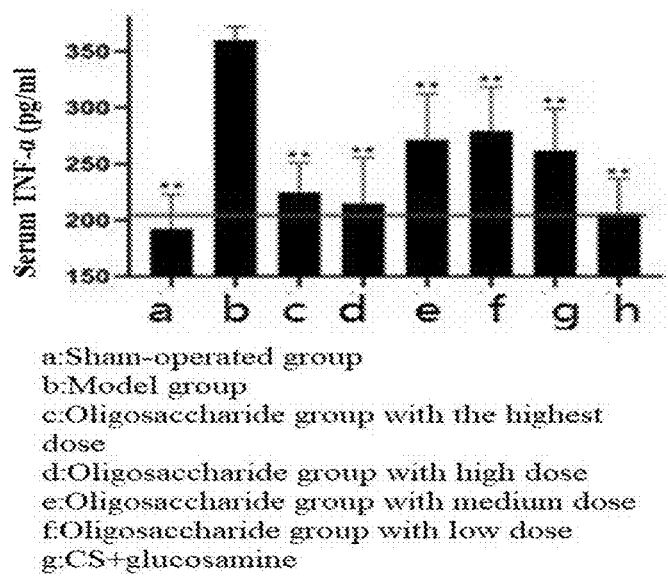
Fig.11D Serum TNF-α in rats

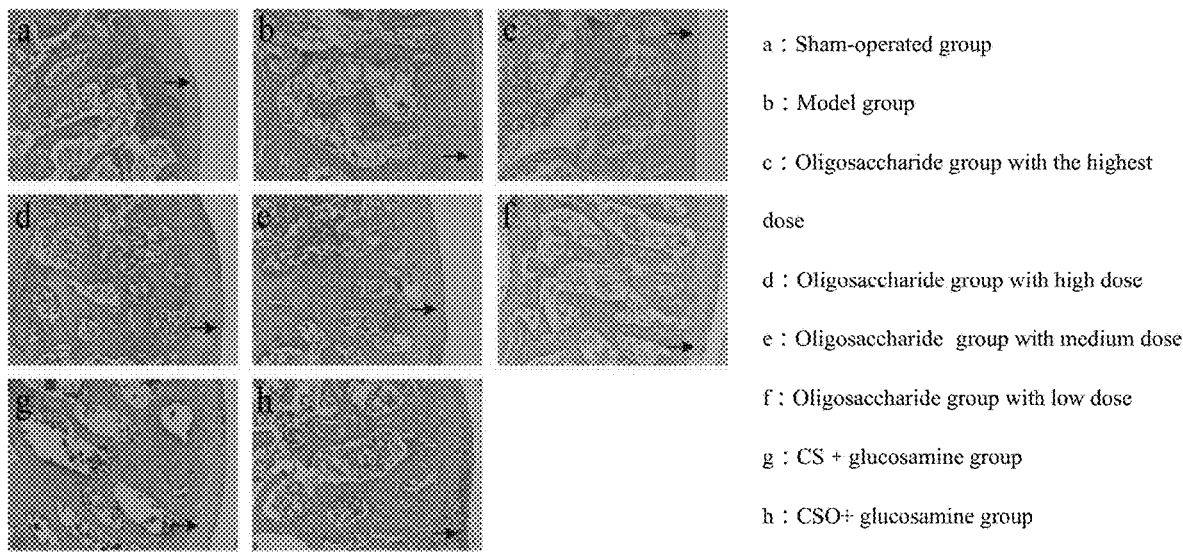

a : Sham-operated group b : Model group c : Oligosaccharide group with the highest dose d : Oligosaccharide group with high dose e : Oligosaccharide group with medium dose f : Oligosaccharide group with low dose g : CS + glucosamine group h : CSO + glucosamine group Fig.11E Pathological staining of knee joint in rats (×100)

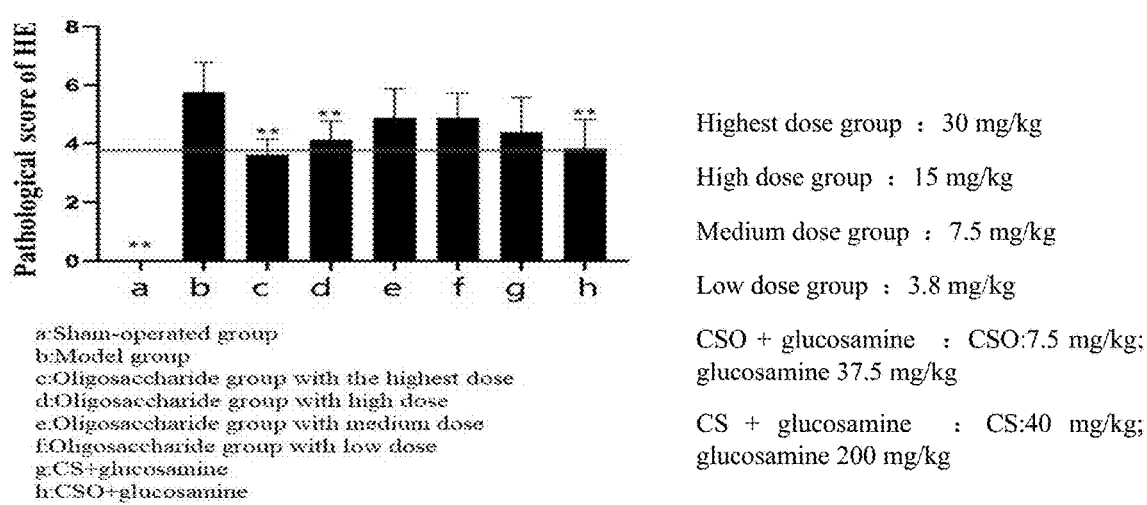

Highest dose group : 30 mg/kg

High dose group : 15 mg/kg

Medium dose group : 7.5 mg/kg

Low dose group : 3.8 mg/kg

CSO + glucosamine : CSO:7.5 mg/kg; glucosamine 37.5 mg/kg

CS + glucosamine : CS:40 mg/kg; glucosamine 200 mg/kg

Fig.11F Pathological score of knee joint in rats

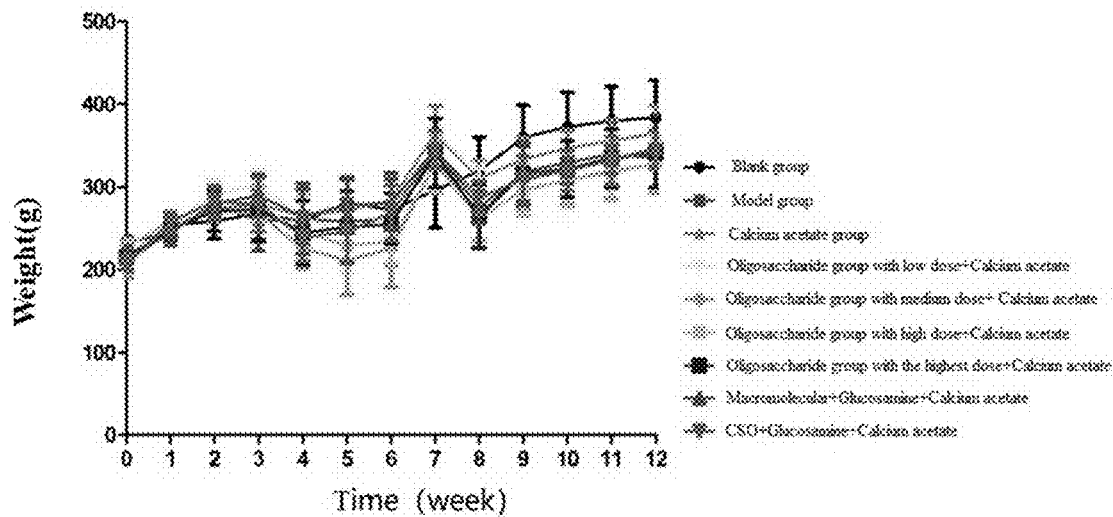
Fig.12A Body weight changes in female rats
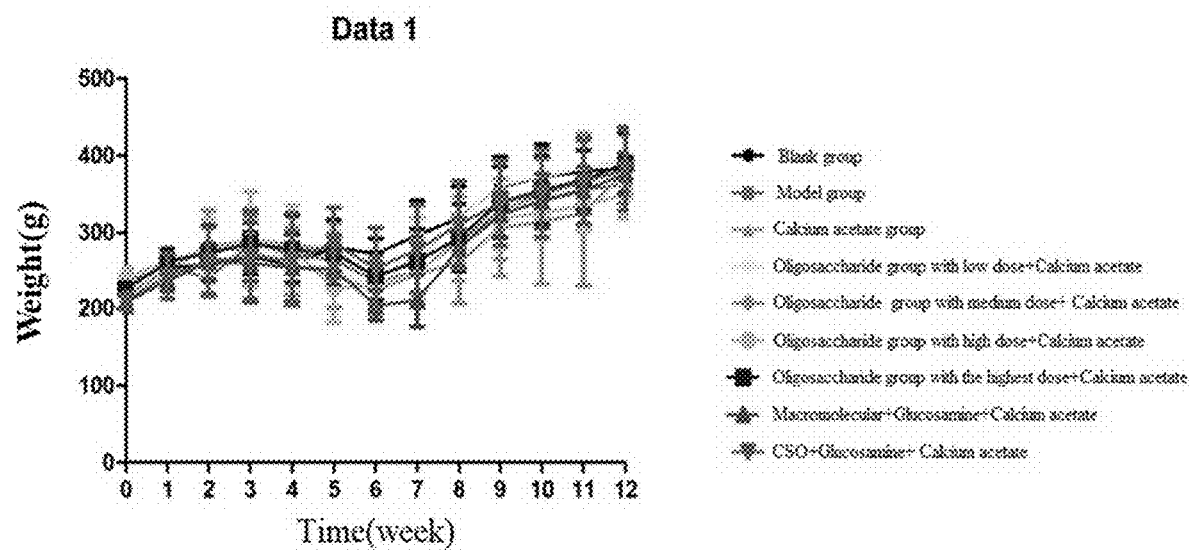
Fig.12B Body weight changes in male rats

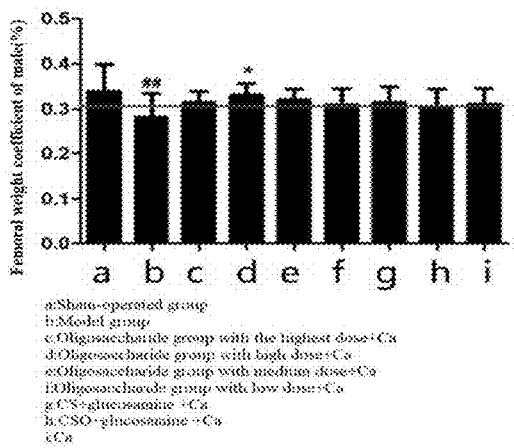 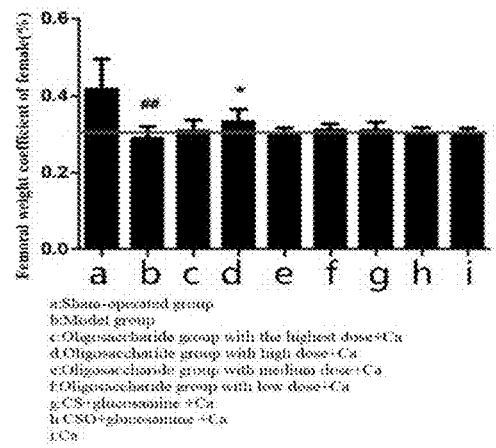

Fig.12C Femoral weight coefficient of male rats

Fig.12D Femoral weight coefficient of female rats

Highest dose group: 30 mg/kg CSO+158 mg/kg Calcium acetate

High dose group: 15 mg/kg CSO+158 mg/kg Calcium acetate

Medium dose group: 7.5 mg/kg CSO+158 mg/kg Calcium acetate

Low dose group: 3.8 mg/kg CSO+158 mg/kg Calcium acetate

CSO + glucosamine: 7.5 mg/kg CSO+37.5 mg/kg glucosamine +158 mg/kg Calcium acetate CS+ glucosamine: 40 mg/kg CS+200 mg/kg glucosamine +158 mg/kg Calcium acetate

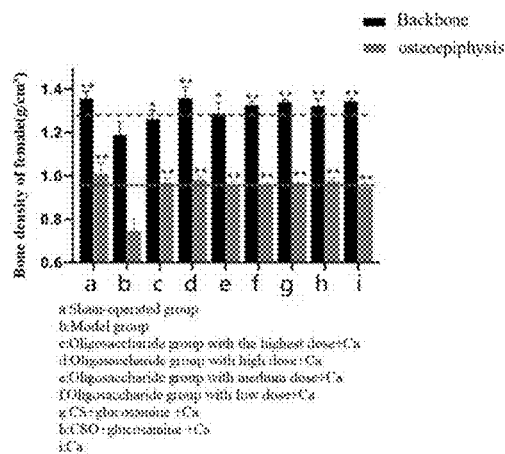
Fig.12E Bone density of female rats
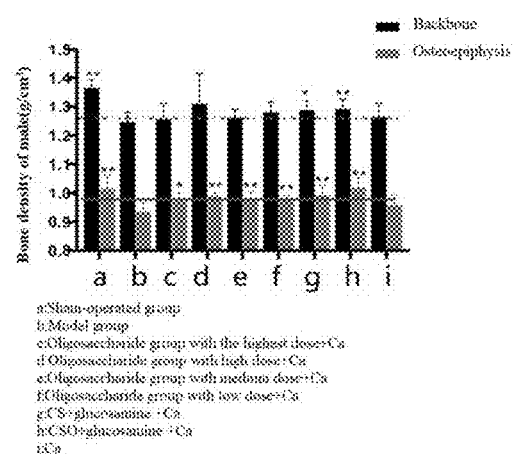
Fig.12F Bone density of male rats
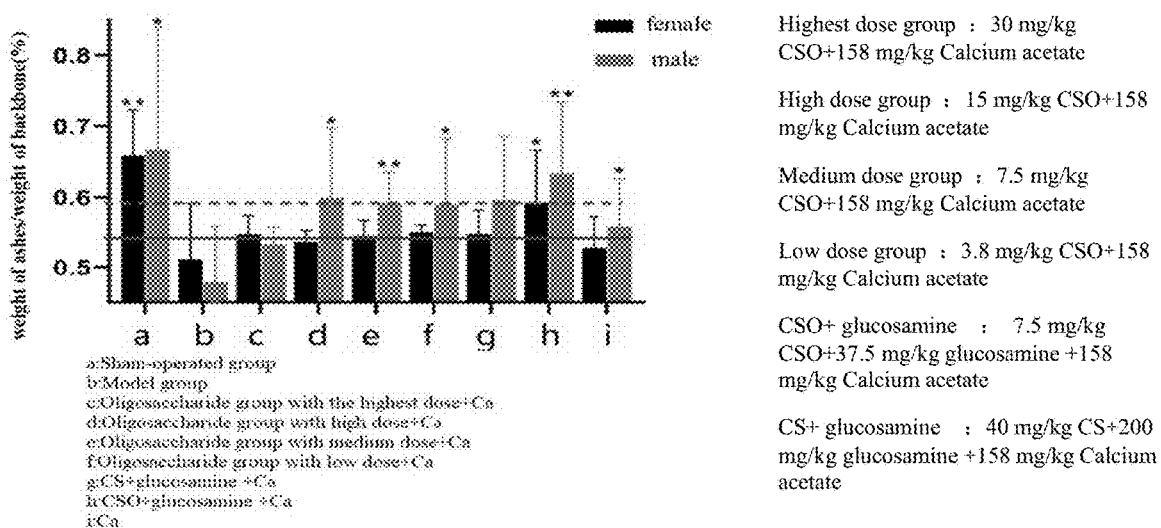
Fig.12G Femoral ashes level in rats

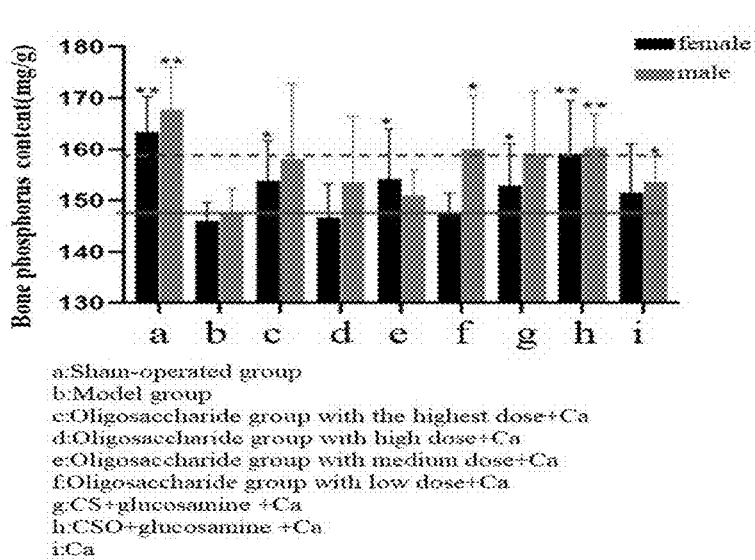

Fig.12H Bone phosphorus level in rats

Highest dose group : 30 mg/kg CSO+158 mg/kg Calcium acetate

High dose group : 15 mg/kg CSO+158 mg/kg Calcium acetate

Medium dose group : 7.5 mg/kg CSO+158 mg/kg Calcium acetate

Low dose group : 3.8 mg/kg CSO+158 mg/kg Calcium acetate

CSO+ glucosamine : 7.5 mg/kg CSO+37.5 mg/kg glucosamine +158 mg/kg Calcium acetate CS+ glucosamine : 40 mg/kg CS+200 mg/kg glucosamine +158 mg/kg Calcium acetate

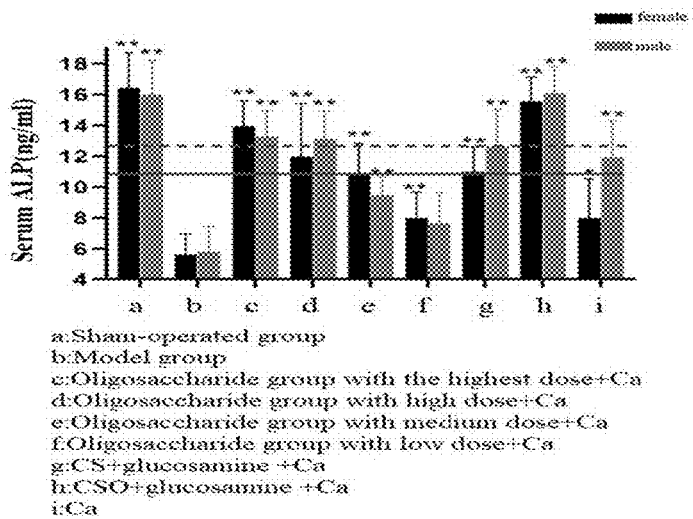

Fig.12I Serum alkaline phosphatase (ALP) level in rats

Highest dose group : 30 mg/kg CSO+158 mg/kg Calcium acetate

High dose group : 15 mg/kg CSO+158 mg/kg Calcium acetate

Medium dose group : 7.5 mg/kg CSO+158 mg/kg Calcium acetate

Low dose group : 3.8 mg/kg CSO+158 mg/kg Calcium acetate

CSO+ glucosamine : 7.5 mg/kg CSO+37.5 mg/kg glucosamine +158 mg/kg Calcium acetate CS+ glucosamine : 40 mg/kg CS+200 mg/kg glucosamine +158 mg/kg Calcium acetate

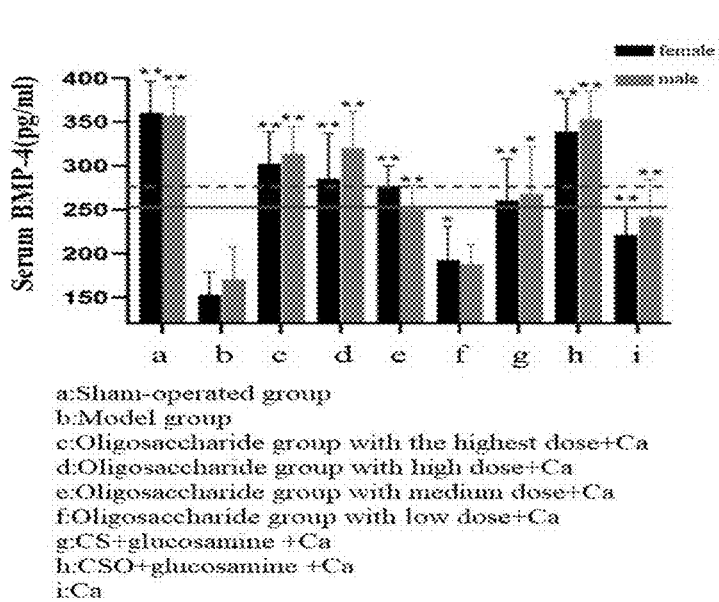
Fig.12J Bone morphogenetic protein-4 (BMP-4) level in serum in rats
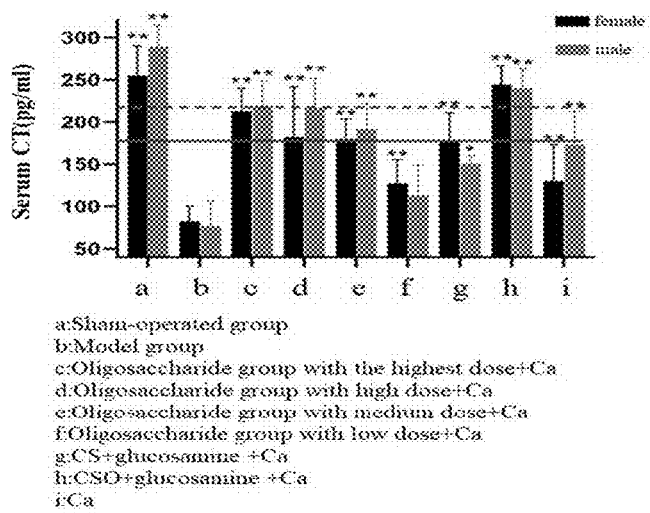
Fig.12K Serum calcitonin (CT) level in rats

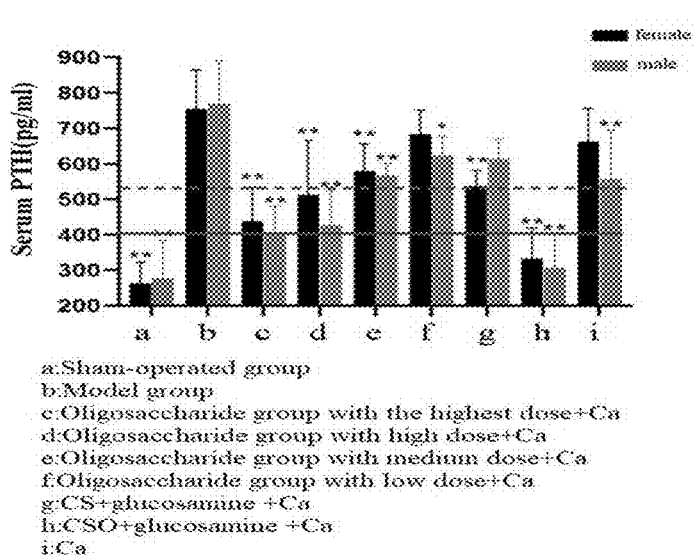

Highest dose group : 30 mg/kg CSO+158 mg/kg Calcium acetate

High dose group : 15 mg/kg CSO+158 mg/kg Calcium acetate

Medium dose group : 7.5 mg/kg CSO+158 mg/kg Calcium acetate

Low dose group : 3.8 mg/kg CSO+158 mg/kg Calcium acetate

CSO+ glucosamine : 7.5 mg/kg CSO+37.5 mg/kg glucosamine +158 mg/kg Calcium acetate CS+ glucosamine : 40 mg/kg CS+200 mg/kg glucosamine +158 mg/kg Calcium acetate Fig.12L Serum parathyroid hormone (PTH) level in rats

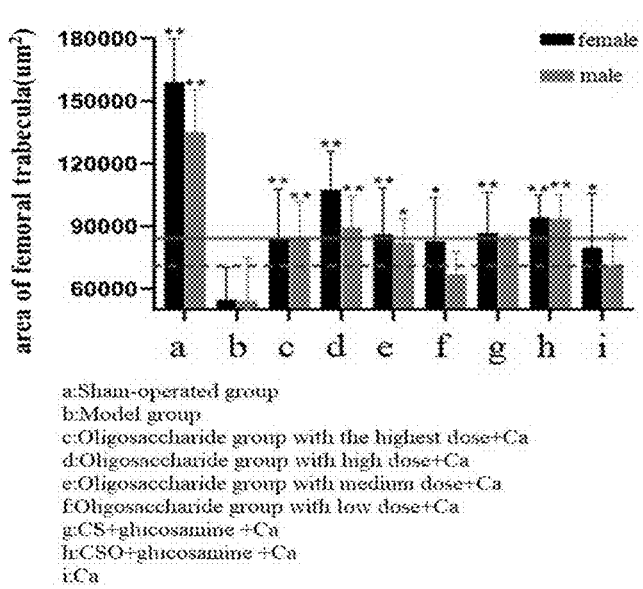

Highest dose group : 30 mg/kg CSO+158 mg/kg Calcium acetate

High dose group : 15 mg/kg CSO+158 mg/kg Calcium acetate

Medium dose group : 7.5 mg/kg CSO+158 mg/kg Calcium acetate

Low dose group : 3.8 mg/kg CSO+158 mg/kg Calcium acetate

CSO+ glucosamine : 7.5 mg/kg CSO+37.5 mg/kg glucosamine +158 mg/kg Calcium acetate CS+ glucosamine : 40 mg/kg CS+200 mg/kg glucosamine +158 mg/kg Calcium acetate Fig.12M The area of femoral trabecula in rats

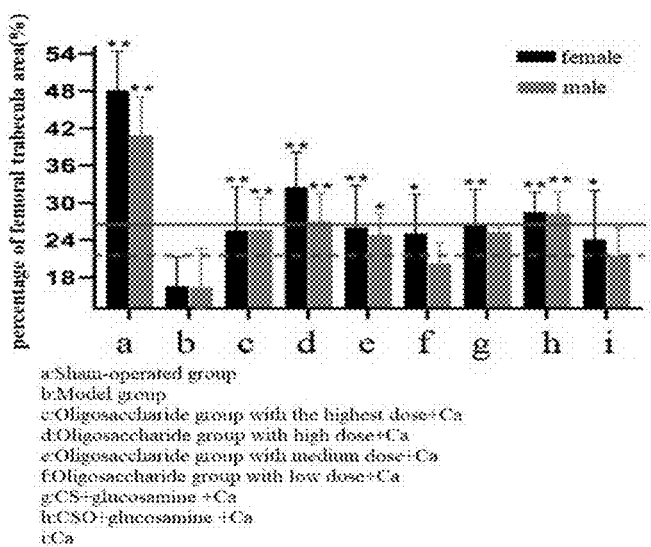

Highest dose group : 30 mg/kg CSO+158 mg/kg Calcium acetate

High dose group : 15 mg/kg CSO+158 mg/kg Calcium acetate

Medium dose group : 7.5 mg/kg CSO+158 mg/kg Calcium acetate

Low dose group : 3.8 mg/kg CSO+158 mg/kg Calcium acetate

CSO+ glucosamine : 7.5 mg/kg CSO+37.5 mg/kg glucosamine +158 mg/kg Calcium acetate CS+ glucosamine : 40 mg/kg CS+200 mg/kg glucosamine +158 mg/kg Calcium acetate Fig.12N The percentage of femoral trabecula area in rats

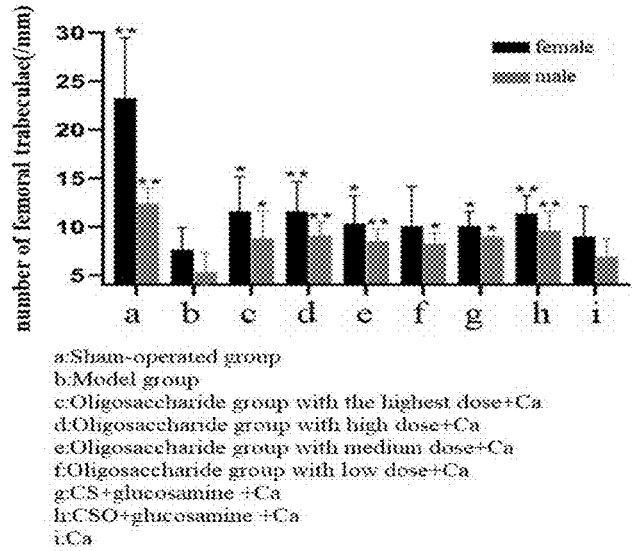

Highest dose group : 30 mg/kg CSO+158 mg/kg Calcium acetate

High dose group : 15 mg/kg CSO+158 mg/kg Calcium acetate

Medium dose group : 7.5 mg/kg CSO+158 mg/kg Calcium acetate

Low dose group : 3.8 mg/kg CSO+158 mg/kg Calcium acetate

CSO+ glucosamine : 7.5 mg/kg CSO+37.5 mg/kg glucosamine +158 mg/kg Calcium acetate CS+ glucosamine : 40 mg/kg CS+200 mg/kg glucosamine +158 mg/kg Calcium acetate Fig.12O Number of femoral trabeculae in rats

LOW MOLECULAR WEIGHT CHONDROITIN SULFATE, COMPOSITION, PREPARATION METHOD AND USE THEREOF

CROSS REFERENCE TO RELATED APPLICATIONS

This application is a continuation of International Application No. PCT/CN2020/126003, filed 2 Nov. 2020, which claims benefit of Chinese Patent Application No. 202011070381.2, filed 30 Sep. 2020; International Application No. PCT/CN2020/079335, filed 13 Mar. 2020; International Application No. PCT/CN2019/115120, filed 1 Nov. 2019, and which applications are incorporated herein by reference. To the extent appropriate, a claim of priority is made to each of the above disclosed applications.

BACKGROUND

Technical Field

The invention relates to the technical field of biochemistry, in particular to a low molecular weight chondroitin sulfate, composition, preparation method and use thereof.

Description of Related Art

Chondroitin sulfate (CS, namely macromolecular chondroitin sulfate or chondroitin sulfate polysaccharide) is a class of linear polysaccharide containing polyanion. D-glucuronic acid (GlcA) and N-acetyl-D-galactosamine (GalNAc) are linked by β-1,3 glycosidic bond to form disaccharide units, which are linked to each other by β-1,4 glycosidic bond, and sulphate groups are introduced at different positions in the subsequent biosynthesis process. Chondroitin sulfate widely exists in the cartilage and connective tissue in various animals.

A large number of studies have shown that CS has the activities of lowering blood lipid, anti-atherosclerosis, enhancing immunity, anti-viral hepatitis and anti-tumor, and has been clinically widely used in the medicine and food fields for orthopedics, ophthalmology, cardiovascular diseases and oral diseases. For example, in the recommendation for the treatment of knee osteoarthritis published by the European League of Rheumatism, CS is considered to be an effective drug for the treatment of knee osteoarthritis; in Japan, CS is prepared as an oral preparation for joint pain relief, or as an eye drop for tear-filling or corneal protection; in the United States, CS is marketed as a dietary supplement; in Australia, CS is mostly prepared into composite preparations and marketed as nutritional supplements; Sodium chondroitin sulfate (CS-Na), CS-Na tablets and CS-Na capsules are also collected in the 2015 edition of the Chinese Pharmacopoeia, and they are classified as drugs for reducing blood lipid and treating bone and joint diseases. Therefore, CS, as a kind of macromolecular substance with diverse biological activities and wide application, has valuable development and utilization value. However, the traditional high molecular weight CS has high apparent viscosity, complex structure and is not easy to pass through the cell membrane. In clinical application, it is mainly faced with the problems of low bioavailability, poor oral absorption and unstable efficacy.

The relative molecular weight (Mr) of natural CS is generally 50-100 kDa, and the Mr range of CS prepared by different processes and sources is generally 10-40 kDa. When the Mr is lower than 10 kDa, it is called as low molecular weight chondroitin sulfate (LMWCS) or chondroitin sulfate oligosaccharide (CSO).

LMWCS is usually prepared by degradation of CS products, including acid hydrolysis, alkaline hydrolysis and enzymatic methods. There are many impurities in the reaction products by acid degradation and they are not easy to be removed. The sulfonic groups on the chondroitin sulfate will also fall off to varying degrees during the reaction, and cause environmental pollution. In contrast, the reaction conditions of enzymatic hydrolysis are mild, and thus the pollution is reduced and easily controlled, and enzymatic hydrolysis will not cause the destruction of sulfonic acid group, which is conducive to industrial production.

According to the prior art of a patent literature CN102676613B, it discloses that the hyaluronidase from bovine testicles has low specificity and low efficiency, and the mixture of chondroitin sulfate disaccharide, tetrasaccharide and hexasaccharide are obtained and then separated into three monomers with molecular weight of 521 Da, 1024 Da and 1527 Da, respectively, which are different in composition and molecular weight from low molecular weight chondroitin sulfate in the present invention. The molecular weight of disaccharide in the present process is about 379 Da and about 459 Da, and the molecular weight of tetrasaccharide is about 838 Da and about 918 Da. In addition, no pharmacodynamic studies of the obtained product have been carried out in the patent literature.

The patent application CN108070627A discloses a use of chondroitin sulfate AC enzyme with a high cost to obtain chondroitin sulfate D tetrasaccharide with a specific structure and molecular weight, but its molecular weight is 1078 Da which is different from the present low molecular weight chondroitin sulfate tetrasaccharide of about 838 Da and about 918 Da. In addition, no pharmacodynamic studies of the obtained product have been carried out in the patent application.

The patent CN103602711B discloses a use of enzyme liquid upon fermentation from *Bacteria sulfolifolia,* which efficiency is low, 1000 L fermentation liquid can only catalyze 400 kg products, the resulting chondroitin sulfate disaccharide has a molecular weight of 450-480 Da, and the content of disaccharide is more than 97%. Different from low molecular weight chondroitin sulfate in composition and molecular weight of the present invention, the molecular weight of disaccharide in the present process is about 379 Da and about 459 Da, and the proportion of disaccharide content is 42-58%. In addition, it discloses in the patent that the products are made from chicken cartilage, pig cartilage and bovine cartilage, and are specifically used for the treatment of myocarditis.

In a periodical literature, "Preparation of Chondroitin Sulfate Oligosaccharides by Enzymatic Method and Its Antioxidant Activity" (Food Industry Science and Technology, 2017,13,48~52.), it discloses a use of chondroitin sulfate enzyme (molecular weight 76 kDa) upon fermentation from the enzyme-producing strain *Acinetobacter* sp.C26. The catalytic efficiency is low, the reaction concentration is only reported as 2%, and the proportion of oligosaccharides is not analyzed. Chondroitin sulfate disaccharides and tetrasaccharides are obtained by pyrolysis. The m/Z of disaccharides is 342 Da and 458 Da, the m/Z of tetrasaccharides is 939 Da, which is different from the molecular weight of disaccharide of about 379 Da and about 459 Da and the molecular weight of the tetrasaccharide of about 838 Da and about 918 Da in the present invention. In addition, the product obtained in this literature has only been tested for antioxidant activity, and no other pharmacodynamic studies have been carried out.

Therefore, the research on the pharmacodynamics of low molecular weight chondroitin sulfate at home and abroad is not sufficient, especially for chondroitin sulfate disaccharide and chondroitin sulfate tetrasaccharide as the main components which have the contents controlled within a certain range and the average molecular weight stably controlled to less than 1000 Dalton and narrow molecular weight distribution. It still needs to further study and identify low molecular weight chondroitin sulfate for the treatment of joint injury, so as to supplement research in the art at home and abroad.

SUMMARY

The invention aims to overcome the above deficiencies in the prior art and provides a novel low molecular weight chondroitin sulfate, composition, preparation method and use thereof.

In order to realize the above objects, one of the objects of the present invention is to provide the following technical solution: a low molecular weight chondroitin sulfate with average molecular weight of less than 1000 Dalton and a narrow molecular weight distribution, comprising chondroitin sulfate disaccharide and chondroitin sulfate tetrasaccharide as main components, of which the content of chondroitin sulfate disaccharide is 43~60% and the content of chondroitin sulfate tetrasaccharide is 30~45%, the sum of chondroitin sulfate disaccharide and chondroitin sulfate tetrasaccharide is more than 87%; the general formula of the structure of the low molecular weight chondroitin sulfate is shown in the following formula I:

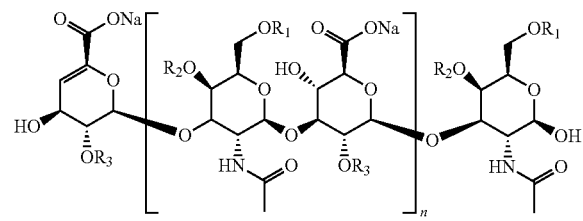

Formula I: n=0~5, and n is an integer, $R_1$, $R_2$, $R_3$=—H or —$SO_3Na$.

Further, the average molecular weight of the low molecular weight chondroitin sulfate is 590~830 Da, and preferably 677~742 Da.

Further, in the low molecular weight chondroitin sulfate, the content of chondroitin sulfate disaccharide is 48-55%, and the content of chondroitin sulfate tetrasaccharide is 35-40%.

The second object of the invention is to provide the following technical solution: a method for preparing the low molecular weight chondroitin sulfate, wherein macromolecular chondroitin sulfate as raw material is hydrolyzed by chondroitin sulfate lyase to obtain a low molecular weight chondroitin sulfate product with the average molecular weight stably controlled to less than 1000 Dalton and a narrow molecular weight distribution, the low molecular weight chondroitin sulfate comprising chondroitin sulfate disaccharide and chondroitin sulfate tetrasaccharide as main components, of which the content of chondroitin sulfate disaccharide is 43~60% and the content of chondroitin sulfate tetrasaccharide is 30~45%, the sum of chondroitin sulfate disaccharide and chondroitin sulfate tetrasaccharide is more than 87%; the general formula of the structure of the low molecular weight chondroitin sulfate is shown in the following formula I:

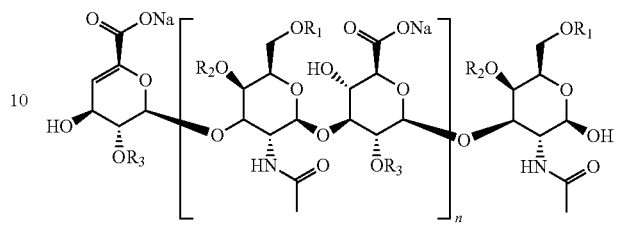

Formula I: n=0~5, and n is an integer, $R_1$, $R_2$, $R_3$=—H or —$SO_3Na$. Further, the chondroitin sulfate lyase is obtained by the following steps: screening and identifying soil samples, sewage or silt from coastal areas, river banks, farmers' markets, slaughterhouses and dining halls, and is optimally expressed by *Escherichia coli* or *Bacillus subtilis*.

Further, the technical method involved is to use commercially available macromolecule chondroitin sulfate as raw material for production, and the raw material is derived from the cartilaginous tissue of terrestrial and marine animals. The raw material further refers to one or more mixtures of chicken cartilage, pig cartilage, bovine cartilage or shark bone, preferably shark bone.

Further, the operating conditions of enzymatic hydrolysis reaction is as follows: the addition amount of the chondroitin sulfate lyase relative to fermentation broth per liter is 100~300 U/L, the concentration of the macromolecular chondroitin sulfate as raw material is 100~700 g/L, the time of enzymatic hydrolysis is 6~40 h, preferably 6~10 h, more preferably 6~8 h, the temperature of enzymatic hydrolysis is 25~35° C., the stirring speed is 100~700 rpm, and the pH of enzymatic hydrolysis is 6.5~8.5. Further, protein is removed from hydrolysate by mixed solvents after enzymolysis reaction, in which the volume ratio of hydrolysate to mixed solvents is 2~5:1, the volume ratio of dichloromethane and isopropyl alcohol in the mixed solvents is 3~5:1, the mixture is stirred at 100~500 rpm for 10~40 min, centrifuged at 3000~5000 rpm for 10~30 min, and the upper reaction solution is taken.

Further, the protein can also be removed from hydrolysate after the enzymatic hydrolysis reaction by ultrafiltration to obtain reaction solution.

Further, the reaction liquid of the upper layer is filtered and sterilized through a 0.22 μm capsule filter after removing the protein, and the reaction solution is added into 8~12 times volume of anhydrous ethanol for precipitation and dried in vacuum.

Further, the reaction solution is filtered and sterilized through a 0.22 μm capsule filter after removing the protein by ultrafiltration and then spray dried.

Further, compared with the macromolecule chondroitin sulfate of shark bone, the low molecular weight chondroitin sulfate obtained by enzymatic hydrolysis of one or more of shark bone and chicken cartilage have more remarkable repair effect at the concentration of 50-100 μg/mL on chondrocytes damaged by 1 mM hydrogen peroxide, and the repair rate is 14%~23%.

Further, the low molecular weight chondroitin sulfate with specific content range of disaccharide and tetrasaccharide can repair chondrocytes damaged by 1 mM hydrogen peroxide in the concentration range of 50~1600 μg/mL, and the repair rate is 20%~62.4%.

Further, the low molecular weight chondroitin sulfate with specific disaccharide and tetrasaccharide content range can repair chondrocytes damaged by 1 mM hydrogen peroxide in the concentration range of 50~1600 μg/mL, and the repair rate is more than 20%, preferably more than 40%, preferably more than 50%, and even preferably more than 60%.

Further, the low molecular weight chondroitin sulfate has applications in the fields of preparing pharmaceuticals, cosmetics, health care products and food.

According to another aspect of the invention, a hydrolyzed chondroitin sulfate composition for increasing bone density and relieving arthritis is provided. The daily dose of hydrolytic chondroitin sulfate and glucosamine composition is lower than the currently known commercially available chondroitin sulfate and glucosamine composition, for example, the daily dose of chondroitin sulfate and glucosamine in Move free is 1700 mg/day; the daily dose of chondroitin sulfate and glucosamine in BJ Tomson is 1160 mg/day. By reducing the dosage, the compliance of taking can be improved, but the effect of increasing bone density and relieving arthritis can not be reduced.

In the following context, glucosamine is sometimes referred to simply as "ammonia sugar".

In this context, the term "hydrolytic chondroitin sulfate" has the same meaning as the term "chondroitin sulfate oligosaccharide (CSO)" and the term "low molecular weight chondroitin sulfate".

The term "hydrolytic chondroitin sulfate" used in this article refers to mixtures of hydrolytic chondroitin sulfate of various molecular weights. For example, the molecular weight can be more than about 300 Da and less than 10000 Da, such as 379-10000 Da, such as more than about 350 Da, more than about 400 Da, more than about 500 Da, more than about 600 Da, more than about 700 Da, more than about 800 Da, more than about 900 Da, lower than about 9000 Da, lower than about 8000 Da, lower than about 7000 Da, lower than about 6000 Da, lower than about 5000 Da, lower than about 4000 Da, lower than about 3000 Da, lower than about 2000 Da, or less than about 1000 Da, preferably less than about 1000 Da of low molecular weight chondroitin sulfate product, more preferably about 590 Da-830 Da, such as about 600 Da-750 Da, and even preferably 677~742 Da.

In one embodiment, the invention provides a hydrolyzed chondroitin sulfate composition, which adopts the following technical proposal: the invention relates to a composition containing hydrolyzed chondroitin sulfate, which is characterized in that it contains a daily dosage of 50 mg~800 mg hydrolyzed chondroitin sulfate for human being. In some embodiments, compositions containing hydrolyzed chondroitin sulfate contain about 50 mg to 800 mg hydrolyzed chondroitin sulfate. In another embodiment, a composition containing hydrolyzed chondroitin sulfate consists of about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg hydrolyzed chondroitin sulfate.

The composition containing hydrolyzed chondroitin sulfate is characterized in that the composition can contain glucosamine.

The invention relates to a composition containing hydrolyzed chondroitin sulfate, which is characterized in that the glucosamine may be a mixture of one or both of glucosamine hydrochloride and glucosamine sulfate.

The composition containing hydrolyzed chondroitin sulfate is characterized in that the hydrolyzed chondroitin sulfate is a mixture of hydrolyzed chondroitin sulfate of various molecular weights.

The composition containing hydrolyzed chondroitin sulfate is characterized in that the ratio of hydrolyzed chondroitin sulfate to glucosamine is about 1:3~1:10,such as about 1:9, about 1:8, about 1:7, about 1:6, about 1:5, about 1:4, about 1:3, preferably about 1:6-1:4, more preferably about 1:5. The composition may contain a human daily dose of about 150 mg~8000 mg glucosamine. In some embodiments, the composition may contain about 7200 mg, about 6400 mg, about 5600 mg, about 4800 mg, about 4000 mg, about 3200 mg, about 2400 mg, about 1600 mg, about 1200 mg, about 800 mg, about 600 mg, about 450 mg, about 400 mg, about 350 mg, about 300 mg, about 250 mg, about 200 mg, about 150 mg glucosamine. The composition more preferably comprises about 100 mg hydrolyzed chondroitin sulfate and about 500 mg glucosamine. The composition may also contain about 200 mg hydrolyzed chondroitin sulfate and about 1000 mg glucosamine.

The invention relates to a hydrolyzed chondroitin sulfate composition, hydrolyzed chondroitin sulfate is a mixture obtained by enzymatic hydrolysis, purification, concentration and spray drying of chondroitin sulfate, and its molecular weight is 379-10000 Da.

The composition containing hydrolyzed chondroitin sulfate also includes pharmaceutical acceptable excipients which are selected from fillers, disintegrants, adhesives, odorants, lubricants and film coating agents.

The invention relates to a hydrolyzed chondroitin sulfate composition and a preparation method thereof, which is characterized in that the fillers include but are not limited to microcrystalline cellulose, starch, dextrin, mannitol, lactose, etc. Disintegration agents include but are not limited to crospovidone, croscarmellose sodium, carboxymethyl starch sodium, hydroxypropyl starch, pregelatinized starch, low substituted-hydroxypropyl cellulose (L-hydroxypropyl cellulose), sodium bicarbonate, citric acid, tartaric acid, etc. Adhesives include but are not limited to carboxymethylcellulose sodium, hydroxypropyl cellulose, methyl cellulose, ethyl cellulose, hydroxypropyl methyl cellulose, polyvinylpyrrolidone, etc. Lubricants include but are not limited to magnesium stearate, silicon dioxide, talc, hydrogenated vegetable oil, polyethylene glycol, stearic acid, etc. The composition of film coating agent includes but is not limited to hydroxypropyl methyl cellulose, polyethylene glycol, colour lake, etc.

The invention relates to a hydrolyzed chondroitin sulfate composition and a preparation method thereof, which is characterized in that the preparation includes but is not limited to tablet, granule, capsule and pill.

The composition of the invention can be used to prepare health care products or medicines for the purpose of reducing arthritis and alleviating pain. In particular, the composition can be used for the preparation of health care products or medicines for reducing osteoarthritis, increasing bone density, improving osteoporosis, or alleviating pain.

The low molecular weight chondroitin sulfate composition or hydrolyzed chondroitin sulfate composition can reduce the levels of inflammatory cytokines IL-6, IL-1β and TNF-α in serum and/or the level of complement C5b-9 in serum.

The low molecular weight chondroitin sulfate composition or hydrolyzed chondroitin sulfate composition can increase the level of hydroxyproline in femur.

Compared with the prior art, the hydrolyzed chondroitin sulfate prepared by enzymatic hydrolysis of chondroitin sulfate can be used to prepare health care products for increasing bone density, improving osteoporosis and alleviating arthritis, and the dosage is low, and the irritation to gastrointestinal tract is less. The human daily dose of hydrolyzed chondroitin sulfate and glucosamine components contained in the composition of the invention is lower than the currently known chondroitin sulfate and glucosamine available on the market. By reducing the dosage, the compliance of taking can be improved, but the effect of increasing bone density and relieving arthritis can not be reduced. To evaluate the pain degree of arthritis in mice and the daily dose of human being, the results showed that the daily dose of hydrolyzed chondroitin sulfate between 50 and 800 mg had obvious relieving and treating effects on the pain of osteoarthritis, and the addition of glucosamine in the composition could increase the relieving and treating effects on the pain of osteoarthritis and osteoporosis.

Compared with the prior art, the invention has the following advantages:
1. Chondroitin sulfate lyase is obtained by screening and identifying soil samples, sewage or sludge from coastal areas, riverside areas, farmers' market, slaughterhouse and dining halls, and optimally expressed by *Escherichia coli* or *Bacillus subtilis,* the chondroitin sulfate lyase is used for enzymatic hydrolysis, which has good specificity and higher enzyme activity. The low molecular weight chondroitin sulfate with average molecular weight less than 1000 Dalton can be stably obtained, especially the low molecular weight chondroitin sulfate with average molecular weight of 590~830 Da, which has narrow molecular weight distribution.
2. Remove protein by solvent method or ultrafiltration method, and the protein content is not more than 0.5%.
3. 100 L fermentation broth catalyzes more than 400 kg macromolecule chondroitin sulfate. It has the advantages of short production cycle, high efficiency and suitable for industrial amplification.
4. The proportion of oligosaccharides of different components is determined by LC-MS analysis. The product quality is stable. The total oligosaccharide content of low molecular weight chondroitin sulfate with disaccharides, tetrasaccharides, hexasaccharides, and octasaccharides is more than 97%, comprising chondroitin sulfate disaccharide and chondroitin sulfate tetrasaccharide as main components, the content of chondroitin sulfate disaccharide is 43~60% and the content of chondroitin sulfate tetrasaccharide is 30~45%, the sum of chondroitin sulfate disaccharide and chondroitin sulfate tetrasaccharide is more than 87%.
5. Compared with the macromolecule chondroitin sulfate of shark bone, the low molecular weight chondroitin sulfate obtained by enzymatic hydrolysis of one or more of shark bone and chicken cartilage has more remarkable repair effect at the concentration of 50-100 μg/mL on chondrocytes damaged by 1 mM hydrogen peroxide, and the repair rate is 14%~23%, which can be used to treat joint injuries. The repair effect of low molecular weight chondroitin sulfate obtained from shark bone is better than that obtained from chicken cartilage, pig cartilage, bovine cartilage and mixed bone. At the concentration of 50 μg/mL, the low molecular weight chondroitin sulfate obtained from shark bone, chicken cartilage, pig cartilage, bovine cartilage and mixed bone has more remarkable repair effect on chondrocytes damaged by 1 mM hydrogen peroxide than the macromolecule chondroitin sulfate obtained from shark bone.

BRIEF DESCRIPTION OF THE DRAWINGS

FIG. 10A shows the effects of various dose groups on the serum concentrations of IL-6(A), IL-1β (B), TNF-α(C) and C5b-9 (D) in mice.

FIG. 10B shows the determination of hydroxyproline (HYP) level in the femur in mice.

FIG. 10C shows the safranin O-fast green staining (×100) in mice knee joint.

FIG. 10D shows the pathological score upon safranin O-fast green staining in mice knee joint.

FIG. 10E shows the C5b-9 immunohistochemical staining (×100) of mice knee joint.

FIG. 10F shows the number of C5b-9 positive cells in mice knee joint.

FIG. 11A shows body weight changes in rats in the study of the dose of CSO in rat osteoarthritis model induced by injection of papain into the knee joint.

FIG. 11B shows the serum IL-6 level in rats in the study of the dose of CSO in rat osteoarthritis model induced by injection of papain into the knee joint.

FIG. 11C shows the serum IL-1β level in rats in the study of the dose of CSO in rat osteoarthritis model induced by injection of papain into the knee joint.

FIG. 11D shows the serum TNF-α level in rats in the study of the dose of CSO in rat of osteoarthritis model induced by injection of papain into the knee joint.

FIG. 11E shows the pathological staining (×100) of the knee joint of rats in the study of the dose of CSO in rat osteoarthritis model induced by injection of papain into the knee joint.

FIG. 11F shows the pathological score in the knee joint of rats in the study of the dose of CSO in rat osteoarthritis model induced by injection of papain into the knee joint.

FIG. 12A shows the body weight changes in rats in the study of the therapeutic effect of CSO on ovariectomy-induced osteoporosis in female rats and testis-induced osteoporosis in male rats.

FIG. 12B shows the body weight changes in male rats in the study of the therapeutic effect of CSO on ovariectomy-induced osteoporosis in female rats and testis-induced osteoporosis in male rats.

FIG. 12C shows the femoral weight coefficient of male rats in the study of the therapeutic effect of CSO on ovariectomy-induced osteoporosis in female rats and testis-induced osteoporosis in male rats.

FIG. 12D shows the femoral weight coefficient of female rats in the study of the therapeutic effect of CSO on ovariectomy-induced osteoporosis in female rats and testis-induced osteoporosis in male rats.

FIG. 12E shows the bone mineral density of female rats in the study of the therapeutic effect of CSO on ovariectomy-induced osteoporosis in female rats and testis-induced osteoporosis in male rats.

FIG. 12F shows the bone mineral density of male rats in the study of the therapeutic effect of CSO on ovariectomy-induced osteoporosis in female rats and testis-induced osteoporosis in male rats.

FIG. 12G shows the femoral ash level in rats in the study of the therapeutic effect of CSO on ovariectomy-induced osteoporosis in female rats and testis-induced osteoporosis in male rats.

FIG. 12H shows the bone phosphorus level in rats in the study of the therapeutic effect of CSO on ovariectomy-induced osteoporosis in female rats and testiectomy-induced osteoporosis in male rats.

FIG. 12I shows the serum alkaline phosphatase (ALP) level in rats in a study of the therapeutic effect of CSO on ovariectomy-induced osteoporosis in female rats and testiectomy-induced osteoporosis in male rats.

FIG. 12J shows the serum level of bone morphogenetic protein-4 (BMP-4) in rats in a study of the therapeutic effect of CSO on ovariectomy-induced osteoporosis in female rats and testiectomy-induced osteoporosis in male rats.

FIG. 12K shows the serum calcitonin (CT) level in rats in a study of the therapeutic effect of CSO on ovariectomy-induced osteoporosis in female rats and testiectomy-induced osteoporosis in male rats.

FIG. 12L shows the serum parathyroid hormone (PTH) level of rats in the study of the therapeutic effect of CSO on ovariectomy-induced osteoporosis in female rats and testiectomy-induced osteoporosis in male rats.

FIG. 12M shows the area of femoral trabecula in rats in the study of the therapeutic effect of CSO on ovariectomy-induced osteoporosis in female rats and testiectomy-induced osteoporosis in male rats.

FIG. 12N shows the percentage of femoral trabecula area in rats in a study of the therapeutic effect of CSO on ovariectomy-induced osteoporosis in female rats and testis-induced osteoporosis in male rats.

FIG. 12O shows the number of femoral trabeculae in rats in a study of the therapeutic effect of CSO on ovariectomy-induced osteoporosis in female rats and testis-induced osteoporosis in male rats.

DESCRIPTION OF THE EMBODIMENTS

Figure 1:
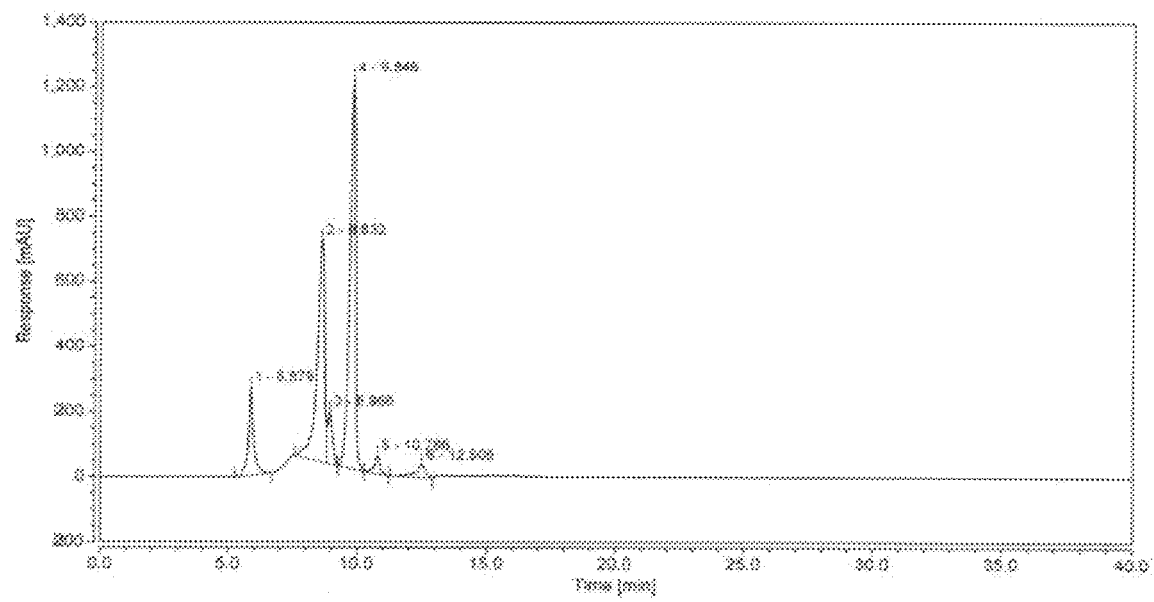
FIG. 1 is an oligosaccharide distribution spectrum of low molecular weight chondroitin sulfate from shark bone in Example 9.

In order to facilitate those skilled in the art to understand the present invention, the technical solutions of the invention will be further described below by reference to the examples, but the following contents should not limit the scope of the invention claimed by the appended claims in any way.

The materials, reagents and the like used in the following examples are commercially available, unless otherwise specified. The chondroitin sulfate lyase is obtained by screening and identifying soil samples, sewage or silt from coastal areas, river banks, farmers' markets, slaughterhouses and dining halls, and optimally expressed by *Escherichia coli* or *Bacillus subtilis*. The highest activity for an enzyme is 11976.5 U/L, and the enzyme contained 998 amino acids, and has a molecular weight of 113 kDa. The amino acid sequence of the chondroitin sulfate lyase is disclosed in another patent application for an invention of the same applicant, with filing date of Apr. 3, 2019, application number of 201910264385.5, publication date of Jun. 21, 2019, and publication number of CN109913437A. All relevant contents of the patent application are introduced into this patent application.

The calculation formula of the average molecular weight of low molecular weight chondroitin sulfate is as follows:

$$\text{Average molecular weight} = \frac{(r_{U_1} \times M_{w_1} + r_{U_2} \times M_{w_2} + r_{U_3} \times M_{w_3} + r_{U_4} \times M_{w_4} + r_{U_5} M_{w_5})}{r_t}$$

Wherein, $r_t = r_{U1} + r_{U2} + r_{U3} + r_{U4} + r_{U5}$.

wherein, $r_{u1}$: the peak response value of component 1 (hexasaccharide and octsaccharide) in the sample solution; $M_{w1}$ is the molecular weight of component 1 in the sample solution;

$r_{u2}$: the peak response value of component 2 (tetrasaccharide) in the sample solution; $M_{w2}$ is the molecular weight of component 2 in the sample solution;

$r_{u3}$: the peak response value of component 3 (tetrasaccharide) in the sample solution; $M_{w3}$ is the molecular weight of component 3 in the sample solution;

$r_{u4}$: the peak response value of component 4 (disaccharide) in the sample solution; $M_{w4}$ is the molecular weight of component 4 in the sample solution;

$r_{u5}$: the peak response value of component 5 (disaccharide) in the sample solution; $M_{w5}$ is the molecular weight of component 5 in the sample solution;

$r_t$: the sum of peak response values of component 1, component 2, component 3, component 4 and component 5 in the sample solution.

The molecular weights of disaccharide (n=0), tetrasaccharide (n=1), hexasaccharide (n=2) and octasaccharide (n=3) in the low molecular weight chondroitin sulfate obtained by enzymatic hydrolysis of macromolecule chondroitin sulfate from shark bone were different. The contents of decosasaccharide (n=4) and dodecosasaccharide (n=5) are very low, so the average molecular weight of oligosaccharide compositions is ignored in the calculation. The molecular weights of disaccharide, tetrasaccharide, hexasaccharide, and octasaccharide, measured by liquid mass spectrometry in the samples obtained in Example 9, are shown in Table 1 below.

TABLE 1

Molecular weight distribution of low molecular weight chondroitin sulfate from shark bone

| # | Disaccharide (Da) | tetrasaccharides (Da) | hexasaccharides (Da) | octasaccharide (Da) |
|---|---|---|---|---|
| 1 | 379.1 and 459.1 | 838.2 and 918.2 | 1155.3 | 1534.5 |

EXAMPLE 1

Enzymatic Hydrolysis Reaction

To 5 L glass beaker was added 2 L purified water, was then added 800 g chondroitin sulfate from shark bone with the stirring speed at 400 rpm. After all the material were dissolved, sodium hydroxide solution was used to adjust the pH to 7.0, and 200 U/L chondroitin sulfate lyase was added. The system was stirred at 30° C. for 6 h to detect whether the average molecular weight was lower than 1000 Da. If the reaction was not complete, the reaction time was extended for another 4 h and continued the central control. The reaction was continued until the average molecular weight was less than 1000 Da.

EXAMPLE 2

Enzymatic Hydrolysis Reaction

To 5 L glass beaker was added 2 L purified water, was then added 400 g chondroitin sulfate from shark bone with the stirring speed at 700 rpm. After all the materials were dissolved, sodium hydroxide solution was used to adjust the pH to 6.5, and 300 U/L chondroitin sulfate lyase was added. The system was stirred at 35° C. for 6 h to detect whether the average molecular weight was lower than 1000 Da. If the reaction was not complete, the reaction time was extended for another 4 h and continued the central control. The reaction was continued until the average molecular weight was less than 1000 Da.

EXAMPLE 3

Enzymatic Hydrolysis Reaction

To 5 L glass beaker was added 2 L purified water, was then added 200 g chondroitin sulfate from shark bone with the stirring speed at 100 rpm. After all the materials were dissolved, sodium hydroxide solution was used to adjust the pH to 8.0, and 100 U/L chondroitin sulfate lyase was added. The system was stirred at 25° C. for 6 h to detect whether the average molecular weight was lower than 1000 Da. If the reaction was not complete, the reaction time was extended for another 4 h and continued the central control. The reaction was continued until the average molecular weight was less than 1000 Da.

EXAMPLE 4

Enzymatic Hydrolysis Reaction

To 5 L glass beaker was added 2 L purified water, controlled the stirring speed to 500 rpm, then added 1400 g chondroitin sulfate from shark bone. After all the materials were dissolved, sodium hydroxide solution was used to adjust the pH to 8.5, and 280 U/L chondroitin sulfate lyase was added. The system was stirred at 28° C. for 6 h to detect whether the average molecular weight was lower than 1000 Da. If the reaction was not complete, the reaction time was extended for another 4 h and continued the central control. The reaction was continued until the average molecular weight was less than 1000 Da.

EXAMPLE 5

Protein Removal

2 L of the hydrolysate after reaction in example 1 was taken and transferred to a centrifuge. The hydrolysate after reaction was centrifuged at 4200 rpm for 15 min to remove the thalli, the supernatant was taken, 0.4 L organic solvent (volume ratio of dichloromethane and isopropyl alcohol=5:1) was added to remove the protein. Upon stirring at 100 rpm for 40 min and centrifugation at 4200 rpm for 15 min, the top layer of the reaction solution was taken out and pour out.

EXAMPLE 6

Protein Removal 2.1 L of the hydrolysate after reaction in example 2 was taken and transferred to a centrifuge. The hydrolysate after reaction was centrifuged at 4200 rpm for 15 min to remove the thalli, the supernatant was taken, 0.7 L organic solvent (volume ratio of dichloromethane and isopropyl alcohol=4:1) was added to remove the protein. Upon stirring at 500 rpm for 10 min and centrifugation at 3000 rpm for 30 min, the top layer of the reaction solution was taken out and pour out.

EXAMPLE 7

Protein Removal

2 L of the hydrolysate after reaction in example 3 was taken and transferred to a centrifuge. The hydrolysate after reaction was centrifuged at 4200 rpm for 15 min to remove the thalli, the supernatant was taken, 1 L organic solvent (volume ratio of dichloromethane and isopropyl alcohol=3:1) was added to remove the protein. Upon stirring at 300 rpm for 30 min and centrifugation at 5000 rpm for 10 min, the top layer of the reaction solution was taken out and pour out.

EXAMPLE 8

Protein Removal 2.3 L of the hydrolysate after reaction in example 4 was taken and ultrafiltered through the ultrafiltration system by a membrane bag with a molecular weight cut-off of 50,000-80,000 in a low temperature condition, so that protein is removed to obtain the ultrafiltration reaction solution.

EXAMPLE 9

Alcohol Precipitation and Drying

The 2 L top layer of the reaction solution obtained from example 5 was filtered and sterilized into the clean area through a 0.22 μm capsule filter. Then the resulting filtrate was dropped into 20 L anhydrous ethanol, stirred for 0.5 h and placed for 2 h. After the solids were completely precipitated, the supernatant was removed. The solids were collected by centrifugal filtration, and then dried in a vacuum drying oven at 45° C. for 24 h until the weight loss was not more than 10%. Then, 650 g low molecular weight chondroitin sulfate product was obtained with a yield of 81.3% (That is, the ratio of 650 g low molecular weight chondroitin sulfate to 800 g chondroitin sulfate as raw material from shark bone). The protein content detected by Coomassie Bright Blue method was 0.3%. The molecular weight distribution was determined by liquid mass spectrometry as shown in FIG. 1, the peak retention time of component 1 was 5.879 min and the content of component 1 was 9.51%, which was mainly composed of hexasaccharide and octasaccharide. The component 2 with the peak retention time of 8.632 min was tetrasaccharide, which content was 33.83%. The component 3 with the peak retention time of 8.966 min was also tetrasaccharide, which content was 5.07%. The component 4 with the peak retention time of 9.846 min was disaccharide, which content was 47.08%. The component 5 with the peak retention time of 10.786 min was also disaccharides, which content was 2.03%. The component 6 with the peak retention time of 12.506 min was salt peak. Therefore, the total content of low molecular weight chondroitin sulfate including disaccharide, tetrasaccharid, hexasaccharide and octasaccharide was 97.52%, comprising disaccharide and tetrasaccharide as main components, in which the sum of disaccharide and tetrasaccharide content was 88.01%. The average molecular weight of the low molecular weight chondroitin sulfate obtained from the enzymatic hydrolysis of shark bone was 704.3~741.2 Da, and specially the calculation was as follows:

Assume that component 1 was all hexasaccharide, then $$\text{average molecular weight} = \frac{(63.802 \times 1155.3 + 227.093 \times 918.2 + 34.008 \times 838.2 + 316.031 \times 459.1 + 13.644 \times 379.1)}{63.802 + 227.093 + 34.008 + 316.031 + 13.644} = 704.3 \ Da$$

Assume that component 1 was all octasaccharide, then $$\text{average molecular weight} = \frac{(63.802 \times 1534.5 + 227.093 \times 918.2 + 34.008 \times 838.2 + 316.031 \times 459.1 + 13.644 \times 379.1)}{63.802 + 227.093 + 34.008 + 316.031 + 13.644} = 741.2 \ Da$$

The molecular weight was analyzed by liquid mass spectrometry (LC-MS) technique in the following specific analysis conditions:

Chromatographic conditions:

Chromatographic column 1: TSK Guard Column SWXL 7 μm, 6 mm×4 cm

Chromatographic column 2: TSK G3000 SWXL 5 μm, 7.8 mm×30 cm

Flow rate: 1 mL/min

Sample amount: 10 μL

Column temperature: 30° C.

Detection wavelength: 195 nm

Collection time: 25 min

Buffer: Diluted 0.38 g ammonium formate with water to 2000 mL, mixed evenly, filtered and got.

Mobile phase: the volume ratio of buffer to methanol was 9:1.

Mass spectrum conditions:

Ion mode: negative ion mode [M–H]–

Fractured voltage: 70V

Mass to charge ratio range: 300-1000 m/z

Dry gas flow rate: 12 L/min

Atomizer pressure: 35 psig

Cap voltage: 3000V.

The results of molecular weight detection were as follows: the corresponding molecular weights of disaccharide were 378.1 and 458.1, and the corresponding molecular weights of tetrasaccharide were 837.2 and 917.1.

EXAMPLE 10

Alcohol Precipitation and Drying

Figure 2:
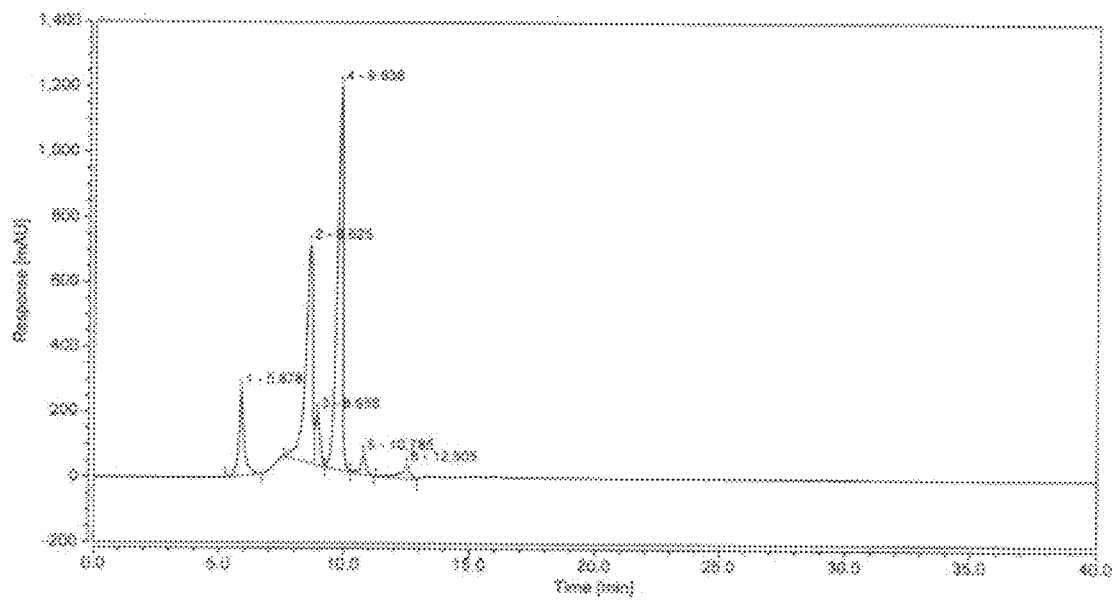
FIG. 2 is an oligosaccharide distribution spectrum of low molecular weight chondroitin sulfate from shark bone in Example 10.

The 2 L top layer of the reaction solution obtained from example 6 was filtered and sterilized into the clean area through a 0.22 μm capsule filter. Then the resulting filtrate was dropped into 16 L anhydrous ethanol, stirred for 0.5 h and placed for 2 h. After the solids were completely precipitated, the supernatant was removed. The solids were collected by centrifugal filtration, and then dried in a vacuum drying oven at 50° C. for 24 h until the weight loss was not more than 10%. Then, 320 g low molecular weight chondroitin sulfate product was obtained with a yield of 80.0% (That is, the ratio of 320 g low molecular weight chondroitin sulfate to 400 g chondroitin sulfate raw material from shark bone). The protein content detected by Coomassie Bright Blue method was 0.4%. The molecular weight distribution was determined by liquid mass spectrometry as shown in FIG. 2, the peak retention time of component 1 was 5.878 min and the content of component 1 was 9.50%, which was mainly composed of hexasaccharide and octasaccharide. The component 2 with the peak retention time of 8.625 min was tetrasaccharide, which content was 33.90%. The component 3 with the peak retention time of 8.958 min was also tetrasaccharide, which content was 5.08%. The component 4 with the peak retention time of 9.838 min was disaccharide, which content was 46.86%. The component 5 with the peak retention time of 10.785 min was also disaccharide, which content was 2.13%. The component 6 with the peak retention time of 12.505 min was salt peak. Therefore, the total content of low molecular weight chondroitin sulfate including disaccharide, tetrasaccharide, hexasaccharide and octasaccharide was 97.47%, mainly disaccharide and tetrasaccharide, in which the sum of disaccharide and tetrasaccharide content was 87.97%. The average molecular weight of the low molecular weight chondroitin sulfate obtained from the enzymatic hydrolysis of shark bone was 704.7-741.6 Da, and the specific calculation process was as follows:

Assume that component 1 was all hexasaccharide, then $$\text{average molecular weight} =$$
$$\frac{(62.295 \times 1155.3 + 222.305 \times 918.2 + 33.314 \times 838.2 + 307.233 \times}{62.295 + 222.305 + 33.314 + 307.223 + 13.949} =$$
$$704.7 \ Da$$

Assume that component 1 was all octasaccharide, then $$\text{average molecular weight} =$$
$$\frac{(62.295 \times 1534.5 + 222.305 \times 918.2 + 33.314 \times 838.2 + 307.233 \times}{62.295 + 222.305 + 33.314 + 307.223 + 13.949} =$$
$$741.6 \ Da$$

EXAMPLE 11

Alcohol Precipitation and Drying

Figure 3:
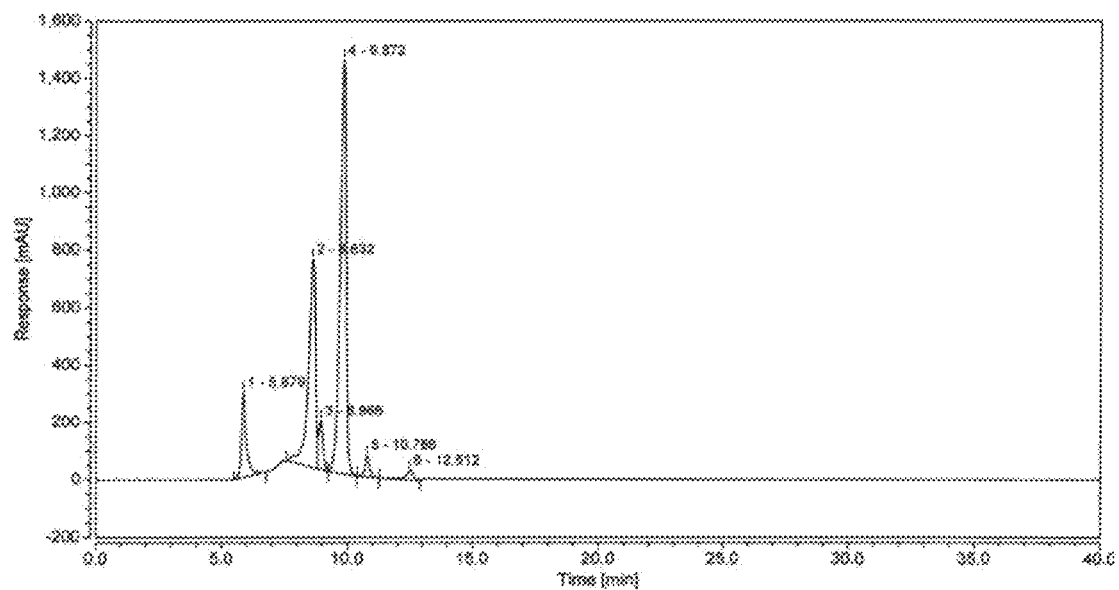
FIG. 3 is an oligosaccharide distribution spectrum of low molecular weight chondroitin sulfate from shark bone in Example 11.

The 2 L top layer of the reaction solution obtained from example 7 was filtered and sterilized into the clean area through a 0.22 μm capsule filter. Then the resulting filtrate was dropped into 24 L anhydrous ethanol, stirred for 0.5 h and placed for 2 h. After the solids were completely precipitated, the supernatant was removed. The solids were collected by centrifugal filtration, and then dried in a vacuum drying oven at 40° C. for 24 h until the weight loss was not more than 10%. Then, 150 g low-molecular weight chondroitin sulfate product was obtained with a yield of 75.0% (That is, the ratio of 150 g low molecular weight chondroitin sulfate to 200 g chondroitin sulfate raw material from shark bone). The protein content detected by Coomassie Bright Blue method was 0.4%. The molecular weight distribution was determined by liquid mass spectrometry as shown in FIG. 3, the peak retention time of component 1 was 5.879 min and the content of component 1 was 8.62%, which was mainly composed of hexasaccharide and octasaccharide. The component 2 with the peak retention time of 8.632 min was tetrasaccharide, which content was 30.79%. The component 3 with the peak retention time of 8.966 min was also tetrasaccharide, which content was 4.41%. The component 4 with the peak retention time of 9.872 min was disaccharide, which content was 52.49%. The component 5 with the peak retention time of 10.786 min was also disaccharides, which content was 2.02%. The component 6 with the peak retention time of 12.512 min was salt peak. Therefore, the total content of low molecular weight chondroitin sulfate including disaccharide, tetrasaccharide, hexasaccharide and octasaccharide was 98.32%, mainly disaccharide and tetrasaccharide, in which the sum of disaccharide and tetrasaccharide content was 89.70%. The average molecular weight of the low molecular weight chondroitin sulfate obtained from the enzymatic hydrolysis of shark bone was 679.2~712.5 Da, and the specific calculation process was as follows:

Assume that component 1 was all hexasaccharide, then $$\text{average molecular weight} =$$
$$\frac{(66.217 \times 1155.3 + 236.598 \times 918.2 + 33.857 \times 838.2 + 403.340 \times}{62.217 + 236.598 + 33.857 + 403.340 + 15.517} =$$
$$679.2 \ Da$$

Assume that component 1 was all octasaccharide, then $$\text{average molecular weight} =$$
$$\frac{(66.217 \times 1534.5 + 236.598 \times 918.2 + 33.857 \times 838.2 + 403.340 \times}{62.217 + 236.598 + 33.857 + 403.340 + 15.517} =$$
$$712.5 \ Da$$

EXAMPLE 12

Spray Drying

Figure 4:
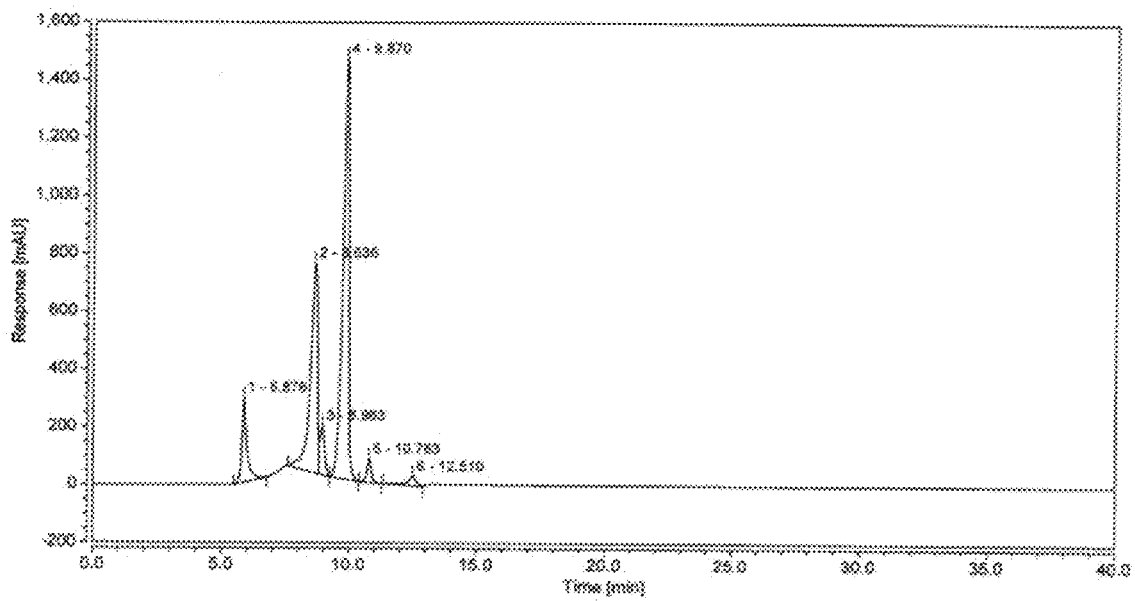
FIG. 4 is an oligosaccharide distribution spectrum of low molecular weight chondroitin sulfate from shark bone in Example 12.

The 2 L top layer of the reaction solution obtained from example 8 was filtered and sterilized into the clean area through a 0.22 μm capsule filter and then spray dried. Spray drying parameters were as follows: inlet air temperature was 120° C., outlet air temperature was 60° C., and flow rate was 100 rpm. Then, 1200 g low-molecular weight chondroitin sulfate product was obtained with a yield of 85.7% (That is, the ratio of 1200 g low molecular weight chondroitin sulfate to 1400 g chondroitin sulfate raw material from shark bone). The protein content detected by Coomassie Bright Blue method was 0.5%. The molecular weight distribution was determined by liquid mass spectrometry as shown in FIG. 4, the peak retention time of component 1 was 5.876 min and the content of component 1 was 8.50%, which was mainly composed of hexasaccharide and octasaccharide. The component 2 with the peak retention time of 8.636 min was tetrasaccharide, which content was 30.59%. The component 3 with the peak retention time of 8.963 min was also tetrasaccharide, which content was 4.43%. The component 4 with the peak retention time of 9.870 min was disaccharide, which content was 52.69%. The component 5 with the peak retention time of 10.783 min was also disaccharide, which content was 2.14%. The component 6 with the peak retention time of 12.510 min was salt peak. Therefore, the total content of low molecular weight chondroitin sulfate including disaccharide, tetrasaccharide, hexasaccharide and octasaccharide was 98.35%, mainly disaccharide and tetrasaccharide, in which the sum of disaccharide and tetrasaccharide content was 89.85%. The average molecular weight of the low molecular weight chondroitin sulfate obtained from the enzymatic hydrolysis of shark bone was 677.4~710.2 Da, and the specific calculation process was as follows:

Assume that component 1 was all hexasaccharide, then $$\text{average molecular weight} =$$
$$\frac{(65.852 \times 1155.3 + 237.083 \times 918.2 + 34.369 \times 838.2 + 408.349 \times}{65.852 + 237.083 + 34.369 + 408.349 + 16.555} =$$
$$677.4 \ Da$$

Assume that component 1 was all octasaccharide, then $$\text{average molecular weight} = $$
$$\frac{\begin{aligned}(65.852 \times 1534.5 + 237.083 \times 918.2 + 34.369 \times 838.2 + 408.349 \times \\ 459.1 + 16.555 \times 379.1)\end{aligned}}{65.852 + 237.083 + 34.369 + 408.349 + 16.555} =$$
$$710.2 \ Da$$

EXAMPLE 13

In accordance with the enzymatic hydrolysis reaction of example 1, the protein removal process of example 5, and the alcohol precipitation and drying process of example 9, another four types of low molecular weight chondroitin sulfate from different sources were obtained by using bovine cartilage, pig cartilage, chicken cartilage and mixed bone chondroitin sulfate of chicken cartilage and shark bone, respectively, with content of 90% from Shandong Baolijiao Company.

EXAMPLE 14

Efficacy and Activity Test (1) Sample Preparation:
(1.1) The sample in example 9 was obtained by the enzymatic hydrolysis reaction process in example 1.
(1.2) Sample of control group 1: a mixture of 0.63 g disaccharide with 97.72% purity and 0.41 g oligomeric peptide from deep sea fish (Ningxia Vanilla Biotechnology Co., Ltd., specification 98%). 61.56% disaccharide and 40.18% oligopeptides from deep sea fish were obtained by calculation.

Figure 8:
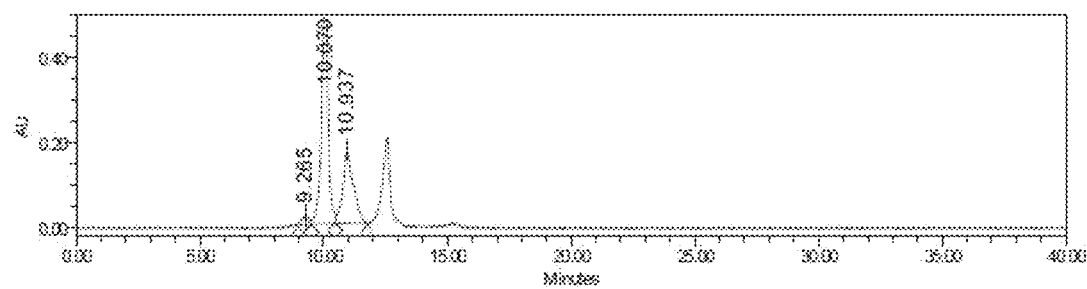
FIG. 8 shows the oligosaccharide distribution spectrum of low molecular weight chondroitin sulfate with 97.72% purity in control group 1.

The preparation process of 97.72% disaccharide samples was as follows:
Mobile phase preparation:
A: 20 mM Tris, adjusted pH to 7.5 by HCl;
B: 20 mM Tris, 1M NaCl, adjusted pH to 7.5 by HCl.
Sample Treatment:
The sample in example 9 was dissolved in mobile phase A by weighting 20 g powder of the sample and dissolving in 1 L of mobile phase A.
Steps: Before purification, Q-Sepharose-FF packing was washed with mobile phase B, and then balanced with mobile phase A. The sample was loaded into Q-Sepharose-FF packing, and the penetration peaks were collected. Tetrasaccharide absorbed in the column were washed with mobile phase B, and the eluted peaks were collected and recirculated for chromatography purification until a single disaccharide peak was detected.
Desalination: The single disaccharide peak detected was combined and collected, and then desalted with a glucose gel column. Before sample loading, the sample was washed with purified water until the conductivity was below 0.1 ms/cm, and the loading sample volume was 20%-30% of the column volume. Then, the peaks with conductivity below 1 ms/cm were collected by washing the column with purified water.
Lyophilized: After the desalted peak was collected and pre-frozen at −20° C., it was put into the freeze-dryer for freeze-drying. After lyophilized to powder, the disaccharide with the purity of 97.72% was collected. The purity of the disaccharide was determined as follows: HPLC was used to determine the molecular weight distribution, as shown in FIG. 8. The component 1 with a peak retention time of 9.265 min was tetrasaccharide with a content of 2.28%. The component 2 with a peak retention time of 10.070 min was disaccharide with a content of 65.79%. The component 3 with a peak retention time of 10.937 min was disaccharide with a content of 31.93%. The salt peak in FIG. 8 has not integrated.

(1.3) Sample of control group 2: Macromolecule chondroitin sulfate of shark bone with 90% content from Shandong Baoliga Company was used, with an average molecular weight of about 70000 Da, which contained almost no disaccharide and tetrasaccharide.

(2) Culture Medium, Solution and Cell Preparation:
(2.1) Basic medium: DMEM/F-12 medium.
(2.2) Growth medium: To 180 mL basal medium was added 20 mL fetal bovine serum (FBS) and stored at 2° C.-8° C.
(2.3) Complete medium: DMEM (Dulbecco's Modified Eagle's medium)+fetal bovine serum cell P5 (5th generation).
(2.4) 1 mM $H_2O_2$ stimulation solution: 30% (9790 mM) hydrogen peroxide was filtered by 0.2 μm sterile filter, and then diluted to 1 mM with basic medium for use.
(2.5) Sample stock solutions 1 and 2: Weighing a certain weight of samples [CSO oligosaccharide from bovine bone (from Example 13), CSO oligosaccharide from pig bone (derived from Example 13), CSO oligosaccharide from shark bone (derived from Example 9), CSO oligosaccharide from chicken bone (from Example 13), CSO oligosaccharide from chicken bone and shark bone (from Example 13) and CSO polysaccharide from shark bone (Shandong Baolijia)]. DPBS was used for diluent to prepare 10 mg/mL sample stock solution 1, and then filtered with 0.2 μm sterile filter membrane for use.

Weighting a certain weight of samples (sample in Example 9, sample in control groups 1~2), DPBS was used for diluent to prepare 10 mg/mL sample stock solution 2, and then filtered with 0.2 μm sterile filter membrane for use.
(2.6) Samples detected in gradient solutions 1 and 2:
The sample solution 1 prepared above was further diluted with basic medium to prepare two dilution series at the concentration of 50 and 100 μg/mL, respectively.
The sample solution 2 prepared above was further diluted with basic medium to prepare seven dilution series at the concentrations ranging from 50 to 3200 μg/mL, namely: 50, 100, 200, 400, 800, 1600 and 3200 μg/mL, respectively.
(2.7) Preparation of cell culture
ATDCS cells were resuscitated with growth medium and incubated in an incubator with humidity, at the temperature of 37±2° C., and at the concentration of carbon dioxide 5±1%. Growth media were used for subculture when about 70% to 90% confluence of cultures was observed with suitable magnification microscopes (such as: 10-40×).

Cell medium was removed for cell passage. The cells was rinsed once with DPBS. Then the cells were infiltrated with about 0.5 mL solution containing 0.25% trypsin for about 1 minute and the cells became round and peeled off the surface. Under the microscope, the morphology of the cells became round, some of the cells broke away from the bottle wall and were immediately added to the complete medium to terminate digestion. Use pipet to suck the medium, blow the cells away from the bottle wall, make the cells evenly dispersed in the medium and transfer the cell suspension into a 15 mL centrifuge tube to centrifuge at 1000 r/m for 5 min. After the centrifuge supernatant was discarded, the cells were resuspended with 2 mL complete medium, then the cells were transferred to 2 new T25 square flasks respectively. In each square flask, 5 mL complete medium was added respectively, mixed gently and placed in an incubator comprising carbon dioxide (37° C., 5% $CO_2$) for culture.

The cells were subcultured within 2-5 days using cell passages between 4-20 and confluence between 70%-90%. According to the procedure of cell culture preparation, an appropriate volume of cell solution containing $2\times10^6$/mL living cells was prepared in the growth medium. A 96-well transparent cell culture plate was taken and 100 μL cell solution was added to each well to make each well contain about 6000 cells. To prevent cell sedimentation and ensure uniformity in each well, mix cell solution frequently when adding cell solution. The plates were incubated in an incubator comprising carbon dioxide (37° C., 5% $CO_2$) overnight (24 h).

After the culture, the next day (24 h), the original medium was discarded, and 50 μL of 1 mM $H_2O_2$ was added into each well (see Step 4.2 for the method for preparing 1 mM $H_2O_2$ stimulation solution). Then, gradient detection solutions of chondroitin sulfate from different sources and at different concentrations were added into each well (see Step 4.3 for method for preparing sample detection gradient solution preparation), and then placed in an incubator comprising carbon dioxide (37° C., 5% $CO_2$) for further culture for 12 hours.

After culture, 10 μL CCK-8 solution was added to each well for another 2 h on the next day (12 h). After the reaction, the absorbance value at 450 nm was detected by a multifunctional enzyme plate analyzer immediately. Two parallel experiments would be tested for each sample, and the average value of light absorption would be taken in the end.

Figure 5:
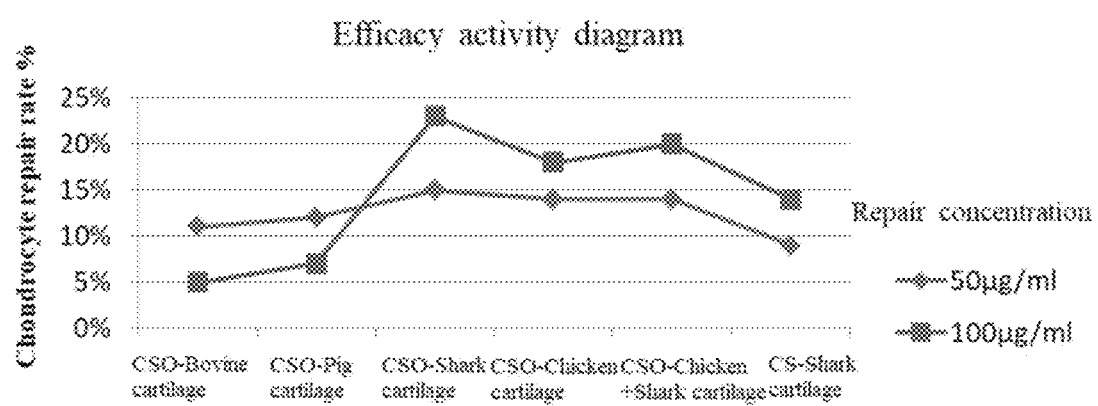
FIG. 5 is the efficacy and activity test results of low molecular weight chondroitin sulfate from different sources in Example 14.

(3) Comparison of Cell Activity between Low Molecular Weight Chondroitin Sulfate from Different Animal Sources and Macromolecule Chondroitin Sulfate:

CCK assay was used to investigate the repair effects on injured chondrocytes for low molecular weight chondroitin sulfate from different animal sources and macromolecule chondroitin sulfate. The results of efficacy test as shown in FIG. 5, the results showed that compared with the macromolecular chondroitin sulfate (chondroitin sulfate polysaccharide) from shark bone, the low molecular weight chondroitin sulfate obtained by enzymatic hydrolysis of one or more of shark bone and chicken bone had more remarkable repair effect at the concentrations of 50~100 μg/mL on chondrocytes damaged by 1 mM hydrogen peroxide, and the repair ability is between 14% and 23%, which could be used for the treatment of joint injury.

(4) Comparison of Cellular Activity between Low Molecular Weight Chondroitin Sulfate from Shark Bone containing Different Components and Macromolecule Chondroitin Sulfate from Shark Bone:

In control group 1, 0.63 g disaccharide with 97.72% purity was mixed with 0.41 g g fish collagen oligopeptide. The content of disaccharide was 61.56% and the content of deep-sea fish oligopeptides was 40.18% by calculation (Ningxia Vanilla Biotechnology Co., Ltd., specification was 98%).

Figure 9:
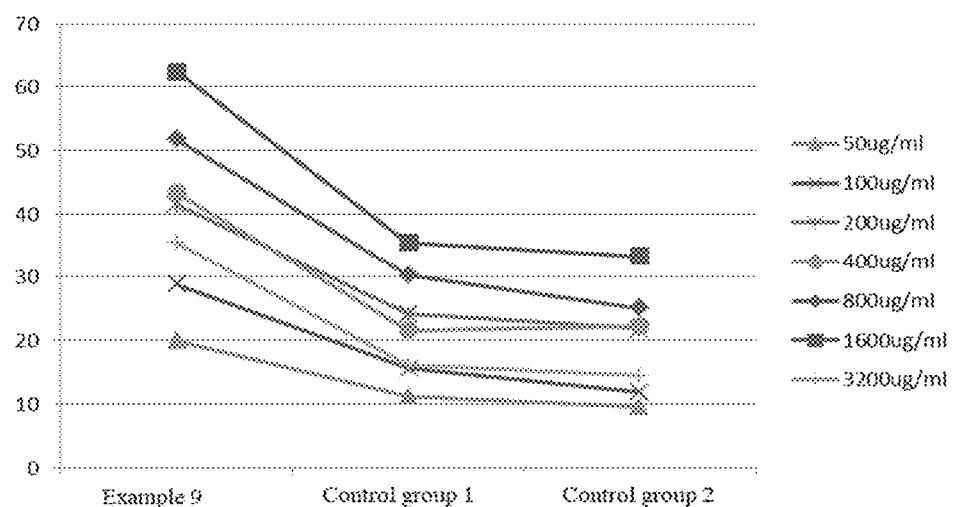
FIG. 9 shows the repair effect of the sample in Example 9 and control groups 1~2 on chondrocytes damaged by 1 mM hydrogen peroxide injury at different concentration levels.

The results are shown in Table A and FIG. 9. The repairing effect of the product of the invention on chondrocytes damaged by 1 mM hydrogen peroxide was more remarkable than that of control groups 1~2 in the concentration range of 50~3200 μg/mL. Among them, the product of the invention had improvement on the repair rate for chondrocytes in the concentration range of 50~1600 μg/mL, and more higher improvement depended on a higher concentration. However, when the concentration reached 3200 μg/mL, the inhibition effect appeared as the concentration was too high, and the repair rate ranged from 20%-62.4%, showing a trend of obvious decline.

TABLE A

| # | Components | 50 μg/ml | 100 μg/mL | 200 μg/mL | 400 μg/mL | 800 μg/mL | 1600 μg/mL | 3200 μg/mL |
|---|---|---|---|---|---|---|---|---|
| Sample of Example 9 | 49.11% disaccharide and 38.90% tetrasaccharide | 20 | 28.9 | 41.5 | 43.4 | 51.8 | 62.4 | 35.5 |
| Control group 1 | 61.56% disaccharide and 40.18% oligopeptides from deep sea fish | 11.3 | 15.6 | 24.2 | 21.6 | 30.4 | 35.5 | 16.1 |
| Control group 2 | Macromolecule chondroitin sulfate from Shark bone (90% content) | 9.6 | 11.8 | 21.9 | 22.3 | 25.1 | 33.3 | 14.5 |

EXAMPLE 15

Hydrolyzed Chondroitin Sulfate Capsules

Prescription:

| Components | Function | Amount |
|---|---|---|
| Hydrolyzed chondroitin sulfate | active substance | 200 g |
| Microcrystalline cellulose | filler | 277 g |
| Crospovidone | disintegrating agent | 15 g |
| Colloidal silicon dioxide | flow aid | 5 g |
| Magnesium stearate | lubricant | 3 g |
| Made into | | 1000 capsules |

Preparation method:

(1) The hydrolyzed chondroitin sulfate from example 9 and microcrystalline cellulose were individually passed through an 80-mesh sieve for ready use;

(2) After the hydrolyzed chondroitin sulfate and microcrystalline cellulose were evenly mixed, the prescribed amount of crospovidone, colloidal silicon dioxide and magnesium stearate were sequentially added, and mixed for 15 min;

(3) Filled the mixture into the capsule shell through the capsule filling machine and formed the capsules.

EXAMPLE 16

Hydrolyzed Chondroitin Sulfate Tablets

Prescription:

| Components | Function | Amount |
|---|---|---|
| Hydrolyzed chondroitin sulfate | active substance | 100 g |
| Microcrystalline cellulose | filler | 352 g |
| Croscarmellose Sodium | disintegrating agent | 15 g |
| Colloidal silicon dioxide | flow aid | 5 g |
| Magnesium stearate | lubricant | 3 g |
| Gastric soluble film coating powder | coating materials | 15 g |
| Made into | | 1000 tablets |

Preparation Method:
(1) The hydrolyzed chondroitin sulfate from example 9 and microcrystalline cellulose were individually passed through an 80-mesh sieve for ready use;
(2) After the hydrolyzed chondroitin sulfate and microcrystalline cellulose were evenly mixed, the prescribed amount of croscarmellose sodium, colloidal silicon dioxide and magnesium stearate were sequentially added, and the mixture was mixed for 15 min;
(3) The mixture was pressed by rotary tablet press, and the hardness of the tablet was controlled to be 6~10 kg;
(4) Coating containing 10% solid content was prepared with purified water;
(5) The tablets were coated by high efficiency coating machine. The inlet air temperature was set at 55° C., the atomization pressure was 0.2 MPa, and the sheet bed temperature was controlled at 40-45° C. After the coating was completed, the tablets were obtained.

EXAMPLE 17

Hydrolyzed Chondroitin Sulfate Tablets

Prescription:

| Components | Function | Amount |
|---|---|---|
| Hydrolyzed chondroitin sulfate | active substance | 50 g |
| Lactose | filler | 402 g |
| Hydroxypropyl cellulose | adhesive | 10 g |
| L-hydroxypropyl cellulose | disintegrating agent | 15 g |
| Colloidal silicon dioxide | flow aid | 5 g |
| Magnesium stearate | lubricant | 3 g |
| Gastric soluble film coating powder | coating materials | 15 g |
| Made into | | 1000 tablets |

Preparation Method:
(1) The hydrolyzed chondroitin sulfate from example 9 and lactose were individually passed through an 80-mesh sieve for ready use;
(2) After the hydrolyzed chondroitin sulfate and lactose were evenly mixed, the prescribed amount of hydroxypropyl cellulose, L-hydroxypropyl cellulose, colloidal silicon dioxide and magnesium stearate were sequentially added, and the mixture was mixed for 15 min;
(3) The mixture was pressed by rotary tablet press, and the hardness of the tablet was controlled to be 6~10 kg;
(4) Coating containing 10% solid content was prepared with purified water;
(5) The tablets were coated by high efficiency coating machine. The inlet air temperature was set at 55° C., the atomization pressure was 0.2 MPa, and the sheet bed temperature was controlled at 40-45° C. After the coating was completed, the tablets were obtained.

EXAMPLE 18

Hydrolyzed Chondroitin Sulfate Tablets

Prescription:

| Components | Function | Amount |
|---|---|---|
| Hydrolyzed chondroitin sulfate | active substance | 25 g |
| Starch | filler | 320 g |
| Dextrin | filler | 100 |
| Hydroxypropyl cellulose | adhesive | 10 g |
| Carboxymethy starch sodium | disintegrating agent | 15 g |
| Colloidal silicon dioxide | flow aid | 5 g |
| Magnesium stearate | lubricant | 5 g |
| Gastric soluble film coating powder | coating materials | 20 g |
| Made into | | 1000 tablets |

Preparation Method:
(1) The hydrolyzed chondroitin sulfate from example 9, starch and dextrin were individually passed through an 80-mesh sieve for ready use;
(2) After the hydrolyzed chondroitin sulfate, starch and dextrin were evenly mixed, the prescribed amount of hydroxypropyl cellulose, carboxymethy starch sodium, colloidal silicon dioxide and magnesium stearate were sequentially added, and the mixture was mixed for 15 min;
(3) The mixture was pressed by rotary tablet press, and the hardness of the tablet was controlled to be 6~10 kg;
(4) Coating containing 10% solid content was prepared with purified water;
(5) The tablets were coated by high efficiency coating machine. The inlet air temperature was set at 55° C., the atomization pressure was 0.2 MPa, and the sheet bed temperature was controlled at 40-45° C. After the coating was completed, the tablets were obtained.

EXAMPLE 19

Hydrolyzed Chondroitin Sulfate Capsules

| Components | Function | Amount |
|---|---|---|
| Hydrolyzed chondroitin sulfate (from example 9) | active substance | 400 g |
| Microcrystalline cellulose | filler | 77 g |
| Carboxymethy starch sodium | disintegrating agent | 15 g |
| Colloidal silicon dioxide | flow aid | 5 g |
| Magnesium stearate | lubricant | 3 g |
| Made into | | 1000 capsules |

EXAMPLE 20

Hydrolyzed Chondroitin Sulfate and Glucosamine Sulfate Tablets

Prescription:

| Components | Function | Amount |
|---|---|---|
| Hydrolyzed chondroitin sulfate (from example 9) | active substance | 50 g |
| Glucosamine sulfate | active substance | 250 g |
| Lactose | filler | 48.6 g |
| Microcrystalline cellulose | filler | 113.4 g |
| Croscarmellose sodium | disintegrating agent | 15 g |
| Colloidal silicon dioxide | flow aid | 5 g |
| Magnesium stearate | lubricant | 3 g |
| Gastric soluble film coating powder | coating materials | 15 g |
| Made into | | 1000 tablets |

Preparation Method:

(1) The hydrolyzed chondroitin sulfate from example 9, glucosamine sulfate, microcrystalline cellulose and lactose were individually passed through an 80-mesh sieve for ready use;

(2) After the hydrolyzed chondroitin sulfate, glucosamine sulfate, microcrystalline cellulose and lactose were evenly mixed, the prescribed amount of Croscarmellose sodium, colloidal silicon dioxide and magnesium stearate were sequentially added, and the mixture was mixed for 15 min;

(3) The mixture was pressed by rotary tablet press, and the hardness of the tablet was controlled to be 6~10 kg;

(4) Coating containing 10% solid content was prepared with purified water;

(5) The tablets were coated by high efficiency coating machine. The inlet air temperature was set at 55° C., the atomization pressure was 0.2 MPa, and the sheet bed temperature was controlled at 40-45° C. After the coating was completed, the tablets were obtained.

EXAMPLE 21

Model Test of Murine Medial Meniscus Instability (DMM) of the Composition Prepared by the Invention 1. Materials 1.1 The tested sample: The composition was prepared according to Examples 15-20 of the present invention, and the recommended daily dosage of the composition in Example 15, Example 16, Example 17, Example 18, Example 19 and Example 20 was 2 tablets (granules)/day, and 1 tablet (granules) in the morning and evening.

1.2 Preparation of test substance: The test sample was mixed into the feed to give. For Examples 15, 16, 17, 18, 19, and 20, 150 mg/day of samples were given to mice daily.

1.3 Administration route of subjects: samples in each Example were given to animals in each group by intragastric administration.

2. Model Building

The mice were anesthetized with chloral hydrate, and the hair of the knee joint of the right hind limb was shaved. After disinfection with iodine and alcohol, an opening with a length of about 1 cm was longitudinally cut off along the side of the inner skeleton of the mice to expose the knee joint. Microsurgical scissors were used to open the articular cavity and the medial meniscus rivet on the tibial plateau was cut off. A 6-0 absorbable suture was used to close the joint capsule. A 6-0 suture was used to close the skin of the joint, and a small amount of penicillin was applied to the sutured skin to prevent infection. The control group (9 mice) was subject to the same procedure, except that the medial meniscus tibial ligament was not cut off On the second day after surgery, DMM mice were randomly divided into 7 groups with 13 rats in each group (1, model control group; 2. Example 15; 3. Example 16; 4. Example 17; 5. Example 18; 6.Example 19; 7. Example 20).

3. Experimental Results

On the second day after operation, mice were given intragastric administration, and the blank group and model group were given the same volume of normal saline by intragastric administration. The animals were given once a day for 12 weeks. The weight of the animals was weighed once a week and the dose was adjusted according to body weight.

Table 1 shows effect of the composition prepared by the present invention on body weight of mice ($(n=13, \bar{x}\pm s)$

| | Blank group | Model group | Example 15 | Example 16 | Example 17 | Example 18 | Example 19 | Example 20 | P values |
|---|---|---|---|---|---|---|---|---|---|
| Composition dosage (mg) | / | / | 150 | 150 | 150 | 150 | 150 | 150 | / |
| Weight at the beginning (g) | 23.97 ± 2.77 | 22.59 ± 2.09 | 22.58 ± 1.58 | 22.37 ± 1.47 | 22.76 ± 1.26 | 22.68 ± 2.88 | 22.66 ± 2.56 | 22.69 ± 2.59 | >0.05 |
| Weight on Week 1 (g) | 24.48 ± 1.98 | 23.50 ± 2.40 | 23.10 ± 1.20 | 22.62 ± 1.78 | 23.33 ± 1.47 | 22.97 ± 2.97 | 23.11 ± 2.61 | 22.68 ± 2.48 | >0.05 |
| Weight on Week 2 (g) | 25.12 ± 2.27 | 23.98 ± 2.32 | 23.62 ± 1.38 | 22.70 ± 2.15 | 23.60 ± 2.00 | 23.40 ± 3.10 | 23.38 ± 3.47 | 22.79 ± 2.64 | >0.05 |
| Weight on Week 3 (g) | 25.98 ± 1.52 | 25.18 ± 2.88 | 24.35 ± 2.45 | 22.98 ± 2.68 | 24.22 ± 2.68 | 23.75 ± 3.45 | 23.95 ± 4.55 | 22.65 ± 2.35 | >0.05 |
| Weight on Week 4 (g) | 26.27 ± 1.77 | 25.56 ± 2.74 | 24.65 ± 2.95 | 23.04 ± 2.84 | 24.45 ± 2.85 | 24.12 ± 3.32 | 24.11 ± 5.29 | 22.88 ± 2.92 | >0.05 |
| Weight on Week 5 (g) | 26.39 ± 1.91 | 25.88 ± 3.18 | 23.97 ± 3.07 | 22.08 ± 2.72 | 24.79 ± 2.71 | 24.48 ± 3.18 | 23.98 ± 1.48 | 23.72 ± 1.78 | >0.05 |
| Weight on Week 6 (g) | 26.60 ± 1.80 | 26.19 ± 3.81 | 24.91 ± 4.11 | 23.11 ± 2.01 | 24.88 ± 3.72 | 25.00 ± 3.00 | 24.47 ± 1.63 | 24.33 ± 2.53 | >0.05 |
| Weight on Week 7 (g) | 26.77 ± 2.03 | 26.61 ± 3.69 | 25.76 ± 3.26 | 23.77 ± 3.57 | 25.26 ± 3.14 | 25.08 ± 2.68 | 25.57 ± 2.13 | 25.00 ± 3.20 | >0.05 |
| Weight on Week 8 (g) | 26.73 ± 1.77 | 26.18 ± 5.02 | 25.99 ± 2.81 | 24.07 ± 2.63 | 25.18 ± 2.22 | 25.71 ± 2.81 | 25.30 ± 2.60 | 24.95 ± 2.65 | >0.05 |

-continued

| | Blank group | Model group | Example 15 | Example 16 | Example 17 | Example 18 | Example 19 | Example 20 | P values |
|---|---|---|---|---|---|---|---|---|---|
| Weight on Week 9 (g) | 26.51 ± 3.51 | 26.57 ± 3.03 | 26.29 ± 2.49 | 24.18 ± 2.28 | 25.76 ± 3.24 | 26.12 ± 1.98 | 25.54 ± 3.56 | 25.19 ± 2.11 | >0.05 |
| Weight on Week 10 (g) | 25.86 ± 1.04 | 26.44 ± 3.76 | 26.12 ± 3.08 | 24.28 ± 1.92 | 25.58 ± 3.42 | 25.71 ± 2.39 | 25.67 ± 3.03 | 25.06 ± 2.34 | >0.05 |
| Weight on Week 11 (g) | 25.84 ± 2.94 | 26.06 ± 4.54 | 25.70 ± 3.10 | 24.09 ± 3.61 | 24.84 ± 3.56 | 25.30 ± 2.70 | 24.73 ± 2.27 | 24.87 ± 2.33 | >0.05 |
| Weight on Week 12 (g) | 26.60 ± 1.70 | 25.94 ± 2.76 | 26.68 ± 2.98 | 24.08 ± 2.92 | 25.38 ± 4.68 | 25.62 ± 3.12 | 24.63 ± 1.83 | 25.54 ± 2.94 | >0.05 |

Figure 6:
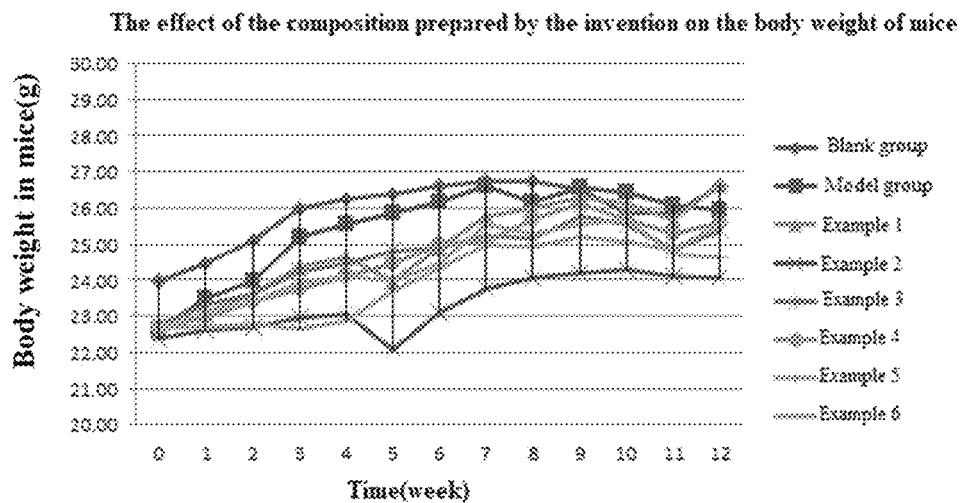
FIG. 6 shows the effect of the composition of the invention on the body weight of mice.

Conclusion: As shown in FIG. 6, from Day 0 of the experiment, the body weight of mice in each group showed a slight increase trend, and there was no significant difference among groups at each time point (P>0.05).

After 12 weeks of intragastric administration in mice, an instrument in YLS-11A channel mode for measuring foot support force in mouse was used to detect the difference of support force for two hind legs of a mouse when standing, so as to evaluate the degree of osteoarthritis pain in mice. Mice were driven into a single channel for a slope climbing experiment with a 60-degree angle. When the mouse started to stand along slope side, the difference in support between the left and right hind legs was recorded. The greater the difference of support force, the more serious the degree of osteoarthritis.

Table 2 shows influence of the composition prepared by the invention on the support force of hind foot of mice (n=13, $\bar{x}$±s)

| | Blank group | Model group | Example 15 | Example 16 | Example 17 | Example 18 | Example 19 | Example 20 |
|---|---|---|---|---|---|---|---|---|
| Difference of foot support force in mice (g) | 0.06 | 7.18 | 3.91 | 3.72 | 3.99 | 4.08 | 3.52 | 3.90 |
| P values | / | <0.01 | <0.01 | <0.01 | <0.05 | <0.05 | <0.01 | <0.01 |

Figure 7:
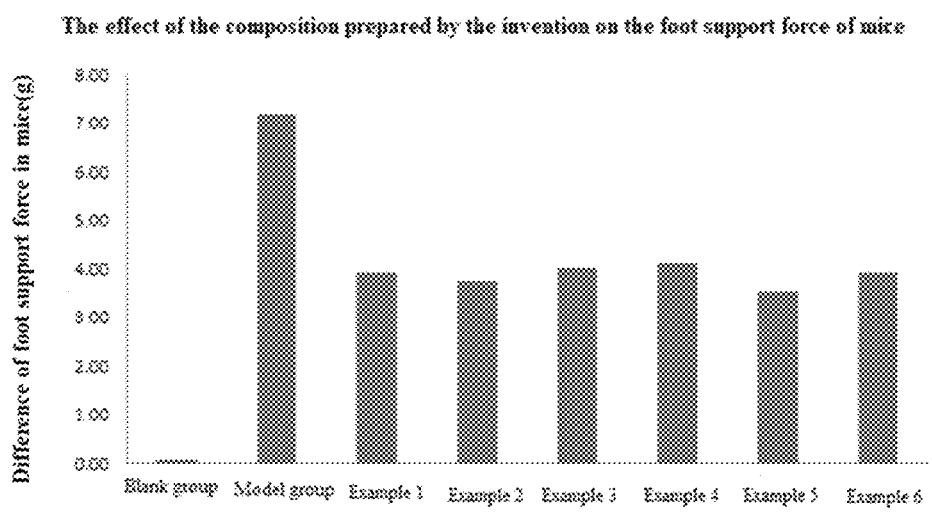
FIG. 7 shows the influence diagram of the composition of the invention on the support force of mice.

The degree of osteoarthritis pain in mice was evaluated by detecting the difference of support force in mice. As shown in FIG. 7, the difference of foot support force in model group was the largest, indicating that the degree of osteoarthritis pain in model group was the most serious. There was a significant difference compared with the sham-operated group, indicating that the model was successfully established. Compared with the model group, Examples 15, 16, 19 and 20 could significantly reduce the difference of foot support force (P<0.01), Examples 17 and 18 also reduced the difference in foot support force (P<0.05). The daily dose of mice can be calculated according to the formula: human dose=mouse dose*body weight/equivalent dose ratio. The human daily dose is calculated as follows:

| Group | Dosing amount of composition in mice (mg/kg/day) | Dosing amount of hydrolyzed chondroitin sulfate in mice (mg/kg/day) | Human dose (mg/day) |
|---|---|---|---|
| Example 15 | 150 | 60 | =60*60/9.1 =400 |
| Example 16 | 150 | 30 | =30*60/9.1 =200 |
| Example 17 | 150 | 15 | =15*60/9.1 =100 |
| Example 18 | 150 | 7.5 | =7.5*60/9.1 =50 |
| Example 19 | 150 | 120 | =120*60/9.1 =800 |
| Example 20 | 150 | 15 | =15*60/9.1 =100 |

Remarks: 1. The equivalent dose ratio of mice to human was 9.1; 2, hydrolyzed chondroitin sulfate dose in mouse=composition dose in mouse*hydrolyzed chondroitin sulfate prescription dose/total tablet weight.

The results showed that the daily dose of hydrolyzed chondroitin sulfate between 50 and 800 mg had remarkable relieving and treating effects on the pain of osteoarthritis, and the addition of glucosamine in the composition could improve the relieving and treating effects on the pain of osteoarthritis.

EXAMPLE 22

To Evaluate the Therapeutic Effect of Chondroitin Sulfate Oligosaccharide (CSO) and a Combination of CSO with Glucosamine (Amino Sugar) on Osteoarthritis Induced by Medial Meniscus Instability (DMM) in Mice by Pathological and Immunohistochemical Detection for Inflammatory Factors, Bone Hydroxyproline Acid and Safranin O-fast Green Staining in Serum C57BL/6 male mice, 8-9 weeks of age, 100 mice, freely drinking and feeding. The mice were anesthetized with chloral hydrate, and the hair of the knee joint of the right hind limb was shaved. The mice were anesthetized with chloral hydrate, and the hair of the knee joint of the right hind limb was shaved. After disinfection with iodine and alcohol, an opening with a length of about 1 cm was longitudinally cut along the side of the inner skeleton of the mice to expose the knee joint. Microsurgical scissors were used to open the articular cavity and the medial meniscus rivet on the tibial plateau was cut off. A 6-0 absorbable suture was used to close the joint capsule. A 6-0 suture was used to close the skin of the joint, and a small amount of penicillin was applied to the sutured skin to prevent infection. The sham-operated group (9 mice) was subject to the same procedure, but the medial meniscus tibial ligament was not cut off.

On the second day after surgery, DMM mice were randomly divided into 7 groups with 13 mice in each group:

1) Model control group;
2) Chondroitin sulfate oligosaccharide group at the highest dose (60 mg/kg);
3) Chondroitin sulfate oligosaccharide group at high dose (30 mg/kg);
4) Chondroitin sulfate oligosaccharide group at medium dose (15 mg/kg) group;
5) Chondroitin sulfate oligosaccharide group at low-dose (7.5 mg/kg);
6) Chondroitin sulfate oligosaccharide (15 mg/kg)+glucosamine hydrochloride (75 mg/kg) group;
7) Macromolecule chondroitin sulfate (CS) (80 mg/kg)+glucosamine (400 mg/kg) group.

On the second day after surgery, mice were given by intragastric administration with an administration volume of 0.2 mL/20 g. The sham-operated group and model group were given with the same volume of normal saline. High molecular weight Chondroitin Sulfate (CS) group (80 mg/kg)+glucosamine (400 mg/kg) was suspended in 0.5% CMC-NA. The animals were given once a day for 12 weeks. The weight of the animals was weighed once a week and the dose was adjusted according to body weight.

Blood samples were collected from eyeballs of mice, and serum was separated. TNF-α, IL-1β, IL-6 and C5b-9 were determined by ELISA. The mice were killed, the right hind femur was taken, and hydroxyprolinic acid in bone was determined according to the kit method. The right knee joint of the hind limb was taken and examined by pathology (safranin O-fast green staining) and C5b-9 expression (immunohistochemistry). The evaluation indicators were summarized as follows:

| Number | Evaluation indicators | Indicators of characterization |
|---|---|---|
| 1 | Rear foot support force difference | To evaluate the severity of osteoarthritis pain in mice. The greater the difference of support force, the more serious the degree of osteoarthritis. |
| 2 | Mechanical pain threshold in mice | To evaluate the severity of osteoarthritis pain in mice. The lower the mechanical pain area in mice, the more severe the degree of osteoarthritis. |
| 3 | Inflammatory cytokine TNF-α level | To evaluate the severity of osteoarthritis in mice, the higher the level of inflammatory factors, the more serious the arthritis. |
| 4 | Inflammatory cytokine IL-1β level | |
| 5 | Inflammatory cytokine IL-6 level | |
| 6 | Complement C5b-9 level | To evaluate the severity of osteoarthritis in mice, the higher the level of complement C5b-9, the more severe the arthritis. |
| 7 | Bone hydroxyprolinic acid | Hydroxyproline in bone was a unique amino acid in bone collagen, which accounts for 90% of bone organics, so hydroxyproline in bone was also the most important component of bone organics. Decrease of hydroxyproline in bone was a major indicator of reduced bone matrix. |
| 8 | Pathological detection | The pathological changes were observed at the histological level. |
| 9 | C5b-9 expression (immunohistochemical) detection | C5b-9 was a product of complement activation that destroyed the cartilage matrix and caused chondrocyte lysis and death, exacerbating osteoarthritis. If the tested substance reduced C5b-9 production, it could reduce cartilage damage in osteoarthritis. |

Influences on the level of inflammatory cytokines in serum

The severity of osteoarthritis in mice was evaluated by measuring the levels of inflammatory cytokines IL-6, IL-1β, TNF-α and complement C5b-9 in serum. As shown in FIG. 10A, the levels of inflammatory cytokines IL-6, IL-1β, TNF-α and complement C5b-9 in model group were the highest, indicating that the model group had the most severe osteoarthritis. There was a significant difference compared with the sham-operated group (P<0.01), indicating that the model was successfully established.

As shown in FIG. 10A, compared with the model group, the levels of inflammatory cytokines IL-6, IL-1β, TNF-α and complement C5b-9 in the highest, high, medium and low dose chondroitin sulfate oligosaccharide groups were decreased to varying degrees, indicating that various doses of chondroitin sulfate oligosaccharide had alleviating and treating effects on osteoarthritis.

Compared with the medium dose group, the levels of inflammatory factors IL-6, IL-1β, TNF-α and complement C5b-9 in serum in CSO+glucosamine group decreased to various degrees, indicating that the combination of chondroitin sulfate oligosaccharide and glucosamine could improve the alleviating and treating effects of osteoarthritis.

Compared with the macromolecule+glucosamine group, the levels of inflammatory factors IL-6, IL-1β, TNF-α and complement C5b-9 in serum in the CSO+glucosamine group and the oligosaccharide group of the invention were significantly decreased, indicating that the effect of chondroitin sulfate oligosaccharide in the treatment of osteoarthritis was better than that of macromolecule+glucosamine group.

Effect on hydroxyproline level in femur

The severity of osteoarthritis in mice was evaluated by detecting hydroxyproline in the femur in the mice. As shown in FIG. 10B, the level of hydroxyproline in the femur in the model group was the lowest, indicating that osteoarthritis in the model group was the most serious. There was a significant difference compared with the sham-operated group (P<0.01), indicating that the model was successfully established.

Compared with model group, the highest, high, medium and low dose chondroitin sulfate oligosaccharide groups and chondroitin sulfate oligosaccharide+glucosamine group significantly increased hydroxyproline level in femur in mice (P<0.01).

Compared with the medium dose group, the level of hydroxyproline in the CSO+glucosamine group was significantly increased, indicating that the combination of glucosamine and CSO could promote the efficacy of the treatment of osteoarthritis.

Compared with the macromolecule+glucosamine group, data of CSO+glucosamine group showed that the effect of CSO was superior to CS.

Pathological examination of knee joint

The severity of osteoarthritis in mice was evaluated by staining the knee joint with safranin O-fast green staining. The results were shown in FIG. 10C and FIG. 10D. The pathological score upon safranin O-fast green staining in the knee joint of mice in the model group was the highest, indicating that the model group had the most severe osteoarthritis. There was a significant difference compared with the sham-operated group ($P<0.01$), indicating that the model was successfully established.

Compared with the model group, chondroitin sulfate oligosaccharide groups at the highest and high dose, and chondroitin sulfate oligosaccharide at medium dose+glucosamine group could significantly reduce the pathological score upon safranin 0-fast green staining ($P<0.05$), indicating that chondroitin sulfate oligosaccharide had the effect of relieving osteoarthritis.

C5b-9 level on cartilage surface of knee joint

The severity of osteoarthritis in mice was evaluated by immunohisto chemical staining in knee joint C5b-9. The results were shown in FIG. 10E and FIG. 10F. The number of C5b-9 positive cells in knee joint of mice in the model group was the highest, indicating that osteoarthritis in the model group was the most serious. There was a significant difference compared with the sham-operated group ($P<0.01$), indicating that the model was successfully established.

Compared with model group, Chondroitin sulfate oligosaccharide group at the highest dose and high dose, oligosaccharide at medium dose+glucosamine group could significantly reduce the number of C5b-9 positive cells in knee joint of mice ($P<0.01$), indicating that chondroitin sulfate oligosaccharide could alleviate cartilage damage in osteoarthritis.

EXAMPLE 23

The Dosage of CSO in Rat Osteoarthritis Model Induced by Papain Injection into Knee Joint Eighty Wistar male rats, 180-220 g. 4% papain and 0.03 mol/L L-cysteine were mixed at a ratio of 2:1 and stood for 30 min. On day 0, 3 and 6 of the experiment, 0.3 mL mixed solution was injected into the knee cavity in rats to induce osteoarthritis model. Normal control group was injected with equal volume of normal saline.

After the last injection of papain mixture, the model animals were randomly divided into 7 groups with 10 rats in each group:
1) Model control group;
2) Chondroitin sulfate oligosaccharide group at the highest dose (30 mg/kg);
3) Chondroitin sulfate oligosaccharide group at high dose (15 mg/kg);
4) Chondroitin sulfate oligosaccharide group at medium dose (7.5 mg/kg);
5) Chondroitin sulfate oligosaccharide group at low-dose (3.8 mg/kg);
6) Chondroitin sulfate oligosaccharide (7.5 mg/kg)+glucosamine hydrochloride (37.5 mg/kg) group;
7) Macromolecule chondroitin sulfate (40 mg/kg)+glucosamine (200 mg/kg) group.

On the second day after modeling, rats were given by intragastric administration with an administration volume of 0.2 mL/100 g. Normal control group and model group were given in the same volume of normal saline. Macromolecule chondroitin sulfate (80 mg/kg)+glucosamine (400 mg/kg) group was suspended in 0.5% CMC-Na. The drug was given once daily for 12 weeks. The animals were weighed every 3 days and the dose was adjusted according to body weight.

The width of both knee joints was measured before modeling, before administration, and at 1, 3, 6, 9, and 12 weeks after administration. The degree of joint swelling was calculated according to the following formula. Degree of joint swelling (mm)=width of knee after inflammation (after administration)—width of knee before inflammation.

After 12 weeks of intragastric administration, blood sample was collected from the abdominal aorta in rats, and serum was separated. TNF-α, IL-1β and IL-6 were determined by ELISA. The femur in the rats was collected and the hydroxyprolinic acid in bone was determined according to the kit method. The knee joint was taken and examined by pathology (HE staining). The evaluation indicators are summarized as follows:

| Number | evaluation indicators | Indicators of characterization |
|---|---|---|
| 1 | Degree of knee swelling | To evaluate the severity of osteoarthritis pain in mice. The greater the Degree of knee swelling, the more serious the degree of osteoarthritis. |
| 2 | Inflammatory cytokine TNF-α level | To evaluate the severity of osteoarthritis in mice, the higher the level of inflammatory factors, the more serious the arthritis. |
| 3 | Inflammatory cytokine IL-1β level | |
| 4 | Inflammatory cytokine IL-6 level | |
| 5 | Bone hydroxyprolinic acid | Bone hydroxyproline was a unique amino acid in bone collagen, which accounts for 90% of bone organics, so bone hydroxyproline was also the most important constituent of bone organics. Decrease of hydroxyproline in bone was a major indicator of reduced bone matrix. |
| 6 | Pathological detection | The pathological changes were observed at the histological level. |
| 7 | C5b-9 expression (immunohistochemical) detection | C5b-9 was a product of complement activation that destroyed the cartilage matrix and caused chondrocyte lysis and death, exacerbating osteoarthritis. If the tested substance reduced C5b-9 production, it could reduce cartilage damage in osteoarthritis. |

As shown in FIG. 11A, from day 0 of the experiment, the body weight of rats in each group showed an increase trend, and there was no significant difference between groups at each time point. The results showed that chondroitin sulfate oligosaccharide had no significant effect on the body weight of rats after 12 weeks.

The severity of osteoarthritis in rats was evaluated by measuring the levels of inflammatory cytokines IL-6, IL-1β and TNF-α in serum in rats. The results were shown in FIG. 11B, FIG. 11C and FIG. 11D. The levels of inflammatory cytokines IL-6, IL-1β and TNF-α in serum in the model group were the highest, indicating that the model group had the most severe osteoarthritis. There was a significant difference compared with the sham-operated group ($P<0.01$), indicating that the model was successfully established.

Compared with the medium dose group, the levels of inflammatory factors IL-6, IL-1β and TNF-α in serum in rats in the medium dose oligosaccharide+glucosamine group decreased to various degrees, indicating that the combination of chondroitin sulfate oligosaccharide and glucosamine could improve the effect of relieving and treating osteoarthritis.

Compared with the macromolecule+glucosamine group, the levels of inflammatory cytokines IL-6, IL-1β and TNF-α in serum in rats in CSO+glucosamine group were significantly decreased, indicating that the effect of chondroitin sulfate oligosaccharide on osteoarthritis was better than that of macromolecule+glucosamine group.

The severity of osteoarthritis in rats was evaluated by pathological examination of the knee joint. The results were shown in FIG. 11E and FIG. 11F. The knee joint pathological score in rats in the model group was the highest, indicating that the osteoarthritis in the model group was the most serious. There was a significant difference compared with the sham-operated group (P<0.01), indicating that the model was successfully established.

Compared with model group, chondroitin sulfate oligosaccharide group at the highest dose and high dose, oligosaccharide medium dose+glucosamine group could significantly reduce pathological score (P<0.01), indicating that chondroitin sulfate oligosaccharide has the effect of relieving osteoarthritis.

EXAMPLE 24

Therapeutic Effect of CSO on Osteoporosis in Ovariectomized Female Rats and Testes Resected Male Rats Female Rats:
Ninety female SD rats weighing 200-220 g were used. The rats adapted to the environment for 3 d. Fasting but freely taking water for 24 hours before surgery. Rats were injected intraperitoneally with 3% chloral hydrate and anesthetised. Ten mice were used as the sham-operated group with longitudinal incisions on the skin and muscle from both sides of the lumbar and dorsal spine without removing the ovaries. For the other animals, longitudinal incisions were made from both sides of the lumbar and dorsal spine to cut the skin and muscle, and both ovaries were removed, and the wounds were sutured. All animals were intramuscular injected with penicillin for 3 consecutive days after operation. (Male rats were operated with the same method to remove testicles).

On the second day after surgery, ovariectomized rats were randomly divided into 8 groups with 8 rats in each group:
1) sham-operated group;
2) Model group;
3) Calcium acetate (158 mg/kg) group;
4) Chondroitin sulfate oligosaccharide group at the highest dose (30 mg/kg)+calcium acetate (158 mg/kg);
5) Chondroitin sulfate oligosaccharide group at high dose (15 mg/kg)+calcium acetate (158 mg/kg);
6) Chondroitin sulfate oligosaccharide group at medium dose (7.5 mg/kg)+calcium acetate (158 mg/kg);
7) Chondroitin sulfate oligosaccharide group with low dose (7.5 mg/kg)+calcium acetate (158 mg/kg);
8) Chondroitin sulfate oligosaccharide (7.5 mg/kg)+glucosamine hydrochloride (37.5 mg/kg)+calcium acetate (158 mg/kg) group;
9) Macromolecule chondroitin sulfate (40 mg/kg)+glucosamine (200 mg/kg)+calcium acetate (158 mg/kg) group.

On the second day after surgery, rats were given by intragastric administration with an administration volume of 0.2 ml/100 g. The sham-operated group and model group were given in the same volume of normal saline. After 12 weeks of continuous administration, the weight of the animals was weighed once a week and the dose was adjusted according to body weight.

24 h after the last administration, blood samples were collected from the orbit in rats. Serum alkaline phosphatase (ALP), bone morphogenetic protein (BGP), parathyroid hormone (PTH) and calcitonin (CT) were determined.

The rats were sacrificed, and the femur on both sides was separated. The right femur was taken and measured for the following indexes: bone weight coefficient (g/100 g body weight), bone density, ash level, bone calcium or bone phosphorus, bone hydroxyproline, HE pathology. The evaluation indicators are summarized as follows:

| Number | Evaluation indicators | Indicators of characterization |
|---|---|---|
| 1 | bone weight coefficient (g/100 g body weight) | The ratio of wet bone weight to body weight reflects bone level. |
| 2 | bone density | It is an important marker of bone quality, and improving bone density can improve osteoporosis. |
| 3 | ash level | It is mainly bone inorganic components, mainly composed of calcium, phosphorus, oxygen andcarbon. |
| 4 | bone calcium or bone phosphorus | An important component in bone minerals. |
| 5 | bone hydroxyproline | Bone hydroxyproline is a unique amino acid in bonecollagen, which accounts for 90% of bone organics, so bone hydroxyproline is also the most important component in bone organics. Decrease of hydroxyproline in bone is amajor indicator of reduced bone matrix. |
| 6 | Pathological detection | The pathological changes were observed at the histological level. |
| 7 | Serum alkaline phosphatase (ALP) | ALP and BGP play an important role in the process of mineralization and are important indicators of bone metastasis rate. |
| 8 | bone morphogenetic protein (BGP) | ALP and BGP play an important role in the process of mineralization and are important indicators of bone metastasis rate. |
| 9 | parathyroid hormone (PTH) | PTH has a bidirectional regulation effect on bone metabolism. High dose of PTH can promote bone resorption and low dose of PTH can promote bone formation. |
| 10 | calcitonin (CT) | The main function of CT is to inhibit bone resorption. The secretion of CT is reduced, thus promoting bone resorption and inhibiting bone formation. |

Note:
Serum ALP, BGP and PTH levels increased, serum CT, bone calcium and bone phosphorus levels decreased significantly. Thus, bone resorption is promoted, bone formation is inhibited, bone mass, bone calcium and bone phosphorus level are reduced, bone mineral loss is significantly increased, and osteoporosis occurs.

Male Rats:
A total of 90 male SD rats weighing 200-220 g were used. The rats adapted to the environment for 3 d. Fasting but freely taking water for 24 hours before surgery. A total of 90 male SD rats weighing 200-220 g were used. The rats adapted to the environment for 3 d. Fasting but freely taking water for 24 hours before surgery. Rats were injected intraperitoneally with 3% chloral hydrate, anesthetised, and scrotal skin was disinfected with horizontal posture, iodine and alcohol. Two longitudinal incisions were made on each side of the mediastinal distance of 1 cm. After cutting the tunica vaginalis, 10 of them separated their bilateral testicles from epididymis (without excision), and then placed back into the scrotum, and the incisions were sutured, which were used as the sham-operated group. In the other 80 testes resected groups, bilateral testes were found and resected in the same way. All animals were intramuscular injected with penicillin for 3 days after operation.

On the second day after surgery, ovariectomized rats were randomly divided into 8 groups with 8 rats in each group:

The remaining steps were the same as those of the female rats.

Results of Experimental

Weight changes

As shown in FIG. 12A and FIG. 12B, from day 0 of the experiment, the body weight of rats in each group showed an increase trend, and there was no significant difference between groups at each time point. The results showed that chondroitin sulfate oligosaccharide had no significant effect on the body weight of female and male rats after 12 weeks of administration.

Bone weight coefficient

As shown in FIG. 12C and FIG. 12D, compared with the sham-operated group, the bone weight coefficient of rats in the model group was significantly decreased (P<0.01), indicating successful modeling. Compared with model group, oligosaccharide high dose group significantly increased bone weight coefficient of female and male rats (P<0.05).

bone mineral density

The severity of osteoporosis was evaluated by detecting the bone mineral density of rats. As shown in FIG. 12E and FIG. 12F, the bone mineral density of rats in the model group was significantly reduced, indicating that the bone mineral density of rats in the model group was the most serious, and there was a significant difference between the model group and the sham-operated group (P<0.01), indicating that the model was successfully established.

Compared with the model group, the BMD of femoral shaft and epiphysis of female osteoporosis rats was significantly increased in each treatment group (P<0.05, P<0.01), indicating that chondroitin sulfate oligosaccharide has the effect of improving osteoporosis.

Compared with the model group, the highest, high, medium, low, CSO+glucosamine group and macromolecule+glucosamine group significantly increased the femoral epiphyseal BMD of male rats (P<0.05, P<0.01); CSO+glucosamine group and macromolecule+glucosamine group significantly increased the bone mineral density of femoral shaft of male rats (P<0.05).

Level of ashes

The severity of osteoporosis in rats was evaluated by measuring the level in femur ashes in the rats. As shown in FIG. 12G, the level of bone ashes in the model group was significantly reduced, indicating that the model group had the most severe osteoporosis, which was significantly different from that in the sham group (P<0.01, P<0.05), indicating that the model was successfully established.

Compared with model group, CSO+glucosamine group significantly increased femoral ashes level of female rats (P<0.05), other administration groups had an increasing trend, and there was no statistical difference (P>0.05). CSO high dose, medium dose and low dose groups, CSO+glucosamine group and Ca group significantly increased the level of femoral ashes in male rats (P<0.01, P<0.05).The results showed that chondroitin sulfate oligosaccharide had the effect of improving osteoporosis.

bone phosphorus

The severity of osteoporosis was evaluated by measuring the bone phosphorus level in rats. As shown in FIG. 12H, the bone phosphorus level in rats in the model group was significantly reduced, indicating that the bone phosphorus level in the model group was the most serious and significantly different from that in the sham-operated group (P<0.01), indicating that the model was successfully established.

Compared with model group, the bone phosphorus level of female rats in CSO highest and medium dose groups, macromolecule+glucosamine group and CSO+glucosamine group significantly increased (P<0.05, P<0.01). CSO low-dose group, CSO+glucosamine group and CA group significantly increased bone phosphorus level in male rats (P<0.05, P<0.01).The results showed that chondroitin sulfate oligosaccharide had the effect of improving osteoporosis.

Serum alkaline phosphatase

Serum alkaline phosphatase (ALP) level in rats was measured to evaluate the severity of osteoporosis. As shown in FIG. 12I, serum alkaline phosphatase level in rats in the model group was significantly decreased, indicating that the model group had the most severe osteoporosis, which was significantly different from the sham-operated group (P<0.01), indicating that the model was successfully established.

Compared with model group, treatment groups significantly increased serum alkaline phosphatase level of female osteoporosis rats (P<0.05, P<0.01). Except for CSO low-dose group, other treatment groups significantly increased serum alkaline phosphatase level of male osteoporosis rats (P<0.01);

Serum level of bone morphogenetic protein-4

Serum level of bone morphogenetic protein-4 (BMP-4) in rats was measured to evaluate the severity of osteoporosis. As shown in FIG. 12J, serum level of bone morphogenetic protein-4 (BMP-4) in rats in the model group was significantly decreased, indicating that the model group had the most severe osteoporosis, which was significantly different from the sham group (P<0.01), indicating that the model was successfully established.

Compared with the model group, the serum BMP-4 level of female osteoporosis rats in all treatment groups was significantly increased (P<0.05, P<0.01). Except for CSO low-dose group, other treatment groups significantly increased serum BMP-4 (P<0.05, P<0.01).

Serum calcitonin

Serum calcitonin (CT) level in rats was measured to evaluate the severity of osteoporosis. As shown in FIG. 12K, serum calcitonin (CT) level in rats in the model group was significantly decreased, indicating that the model group had the most severe osteoporosis, which was significantly different from the sham-operated group (P<0.01), indicating that the model was successfully established.

Compared with the model group, the serum CT level of female osteoporosis rats in each administration group was significantly increased (P<0.05, P<0.01). Except for CSO low-dose group, the serum CT of male osteoporosis rats in other administration groups was significantly increased (P<0.05, P<0.01).

Serum parathyroid hormone

Serum parathyroid hormone (PTH) level in rats was measured to evaluate the severity of osteoporosis. As shown in FIG. 12L, serum PTH level in rats in the model group was significantly decreased, indicating that the model group had the most severe osteoporosis, which was significantly different from that in the sham-operated group (P<0.01), indicating that the model was successfully established.

Compared with model group, except for CSO low-dose group and CA group, other administration groups significantly decreased serum PTH level of female osteoporosis rats (P<0.05, P<0.01). Except for the macromolecule+glucosamine group, other administration groups significantly decreased serum PTH level of male osteoporosis rats (P<0.05, P<0.01).

Femoral trabecula area, percentage of trabecula area and number of trabeculae

To evaluate the severity of osteoporosis, femoral trabecula area, percentage of trabecula area and number of trabeculae in rats were measured. The results was shown in FIG. 12M, FIG. 12N and FIG. 12O, femoral trabecular area, percentage of trabecular area and number of rats in the model group were significantly reduced, indicating that the rats in the model group had the most severe osteoporosis. It was significantly different from sham-operated group (P<0.01), indicating that the model was successfully established.

Compared with the model group, the highest, high and medium dose groups and the oligosaccharide medium dose+ glucosamine group significantly increased femoral trabecular area and percentage of trabecular area of male osteoporosis rats (P<0.05, P<0.01). Compared with model group, treatment groups significantly increased femoral trabecular area and percentage of femoral trabecular area in female osteoporosis rats (P<0.05, P<0.01).

Compared with model group, the number of femoral trabeculae in male osteoporosis rats was significantly increased in all administration groups except Ca group (P<0.05, P<0.01). Compared with model group, except for CSO low-dose group and Ca group, the number of femoral trabeculae in female osteoporosis rats was significantly increased in all treatment groups (P<0.05, P<0.01).

These results indicated that chondroitin sulfate oligosaccharide had the effect of alleviating osteoporosis.

According to the existing experimental data, the following conclusions could be drawn as follow: various doses of chondroitin sulfate oligosaccharide had the effect of relieving and treating the pain of osteoarthritis and osteoporosis. Chondroitin sulfate oligosaccharide combined with glucosamine could improve the effect of relieving and treating osteoarthritis pain and osteoporosis. The effect of chondroitin sulfate oligosaccharide on osteoarthritis and osteoporosis was better than that of macromolecule chondroitin sulfate.

Each of the references cited above throughout the specification application was incorporated herein by reference. In the event of a conflict between the foregoing description and the references, the description provided herein shall prevail.

What is claimed is:
1. A low molecular weight chondroitin sulfate, wherein the average molecular weight of the low molecular weight chondroitin sulfate is less than 1000 Dalton comprising chondroitin sulfate disaccharide and chondroitin sulfate tetrasaccharide as main components, of which the content of chondroitin sulfate disaccharide is 48~55% and the content of chondroitin sulfate tetrasaccharide is 30~45%, the sum of chondroitin sulfate disaccharide and chondroitin sulfate tetrasaccharide is more than 87%; and wherein the general formula of the structure of the low molecular weight chondroitin sulfate is shown in the following formula I:

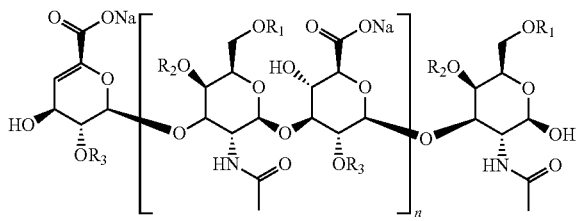

Formula I wherein n=0~5, and n is an integer, $R_1$, $R_2$, $R_3$=—H or —$SO_3Na$.

2. The low molecular weight chondroitin sulfate according to claim 1, wherein the average molecular weight of the low molecular weight chondroitin sulfate is 590~830 Da.

3. The low molecular weight chondroitin sulfate according to claim 1, wherein compared with the macromolecule chondroitin sulfate from shark bone, the low molecular weight chondroitin sulfate obtained by enzymatic hydrolysis of one or more of shark bone and chicken cartilage has a repair rate of about 14-23% at the concentration of 50-100 μg/mL on chondrocytes damaged by 1 mM hydrogen peroxide; or the low molecular weight chondroitin sulfate with specific content range of disaccharide and tetrasaccharide mentioned in claim 1 in the concentration range of 50~1600 μg/mL can repair chondrocytes damaged by 1 mM hydrogen peroxide, and the repair rate is 20%~62.4%.

4. The low molecular weight chondroitin sulfate according to claim 1, wherein the low molecular weight chondroitin sulfate is used in the fields of preparing pharmaceuticals, cosmetics, health care products and food.

5. A composition comprising the low molecular weight chondroitin sulfate according to claim 1, wherein the composition contains at least 50 mg~800 mg of hydrolyzed chondroitin sulfate based on a daily dosage for human being.

6. The composition containing hydrolyzed chondroitin sulfate according to claim 5, wherein the composition contains glucosamine.

7. The composition containing hydrolyzed chondroitin sulfate according to claim 6, wherein the glucosamine is selected from the group consisting of: glucosamine hydrochloride, glucosamine sulfate or a mixture thereof.

8. The composition containing hydrolyzed chondroitin sulfate according to claim 5, wherein the hydrolyzed chondroitin sulfate is a mixture of hydrolyzed chondroitin sulfate with various molecular weights.

9. The composition containing hydrolyzed chondroitin sulfate according to claim 8, wherein the average molecular weight of hydrolyzed chondroitin sulfate is 590-830 Da.

10. The composition containing hydrolyzed chondroitin sulfate according to claim 5, wherein the composition comprises pharmaceutically acceptable excipients selected from fillers, disintegrants, adhesives, odorants, lubricants and film coating agents.

11. The composition containing hydrolyzed chondroitin sulfate according to claim 10, wherein the fillers are selected from the group consisting of microcrystalline cellulose, starch, dextrin, mannitol, lactose; wherein the disintegrants are selected from the group consisting of crospovidone, croscarmellose sodium, carboxymethyl starch sodium, hydroxypropyl starch, pregelatinized starch, low substituted hydroxypropyl cellulose, sodium bicarbonate, citric acid, tartaric acid; wherein the adhesives are selected from the group consisting of carboxymethylcellulose sodium, hydroxypropyl cellulose, methyl cellulose, ethyl cellulose, hydroxypropyl methyl cellulose, polyvinylpyrrolidone; wherein lubricants are selected from the group consisting of magnesium stearate, colloidal silicon dioxide, talc, hydrogenated vegetable oil, polyethylene glycol, stearic acid; and wherein the film coating agents are selected from the group consisting of hydroxypropyl methyl cellulose, polyethylene glycol and colour lake.

12. The composition containing hydrolyzed chondroitin sulfate according to claim 5, wherein the composition is in the dosage forms are selected from the group consisting of tablets, granules capsules and pills.

13. A method for reducing joint inflammation, relieving pain and relieving and treating osteoporosis, comprising administrating an effective amount of the composition containing hydrolyzed chondroitin sulfate according to claim 5 to a subject in need thereof.

14. A method for preparing the low molecular weight chondroitin sulfate according to claim 1, the method comprising: hydrolyzing a macromolecular chondroitin sulfate as raw material with a chondroitin sulfate lyase; obtaining a low molecular weight chondroitin sulfate product with the average molecular weight stably controlled to less than 1000 Dalton; wherein the low molecular weight chondroitin sulfate comprises of a chondroitin sulfate disaccharide and a chondroitin sulfate tetrasaccharide as main components, of which the content of chondroitin sulfate disaccharide is 48~55% and the content of chondroitin sulfate tetrasaccharide is 30~45%, the sum of chondroitin sulfate disaccharide and chondroitin sulfate tetrasaccharide is more than 87%; and wherein the general formula of the structure of the low molecular weight chondroitin sulfate is shown in the following formula I:

Formula I

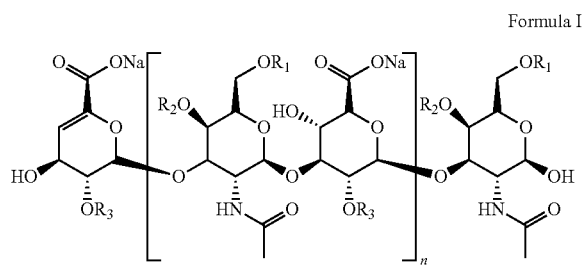

wherein n=0~5, and n is an integer, $R_1$, $R_2$, $R_3$=—H or —$SO_3Na$.

15. The method for preparing the low molecular weight chondroitin sulfate according to claim 14, wherein the chondroitin sulfate lyase is obtained by the following steps: screening and identifying chondroitin sulfate lyase from: soil samples, sewage or silt from coastal areas, riverbanks, farmers' markets, slaughterhouses and dining halls, and expressing said chondroitin sulfate lyase in *Escherichia coli* or *Bacillus subtilis*.

16. The method for preparing the low molecular weight chondroitin sulfate according to claim 14, wherein the macromolecule chondroitin sulfate as raw material is derived from the cartilaginous tissue of terrestrial and marine animals selected from one or more of chicken cartilage, pig cartilage, bovine cartilage or shark bone.

17. The method for preparing the low molecular weight chondroitin sulfate according to claim 16, wherein the macromolecule chondroitin sulfate as raw material is derived from shark bone.

18. The method for preparing the low molecular weight chondroitin sulfate according to claim 14, wherein the operating conditions of the enzymatic hydrolysis reaction are as follows: the addition amount of the chondroitin sulfate lyase relative to fermentation broth per liter is 100~300 U/L, the concentration of the macromolecule chondroitin sulfate as raw material is 100~700 g/L, the time of enzymatic hydrolysis is 6~10 h, the temperature of enzymatic hydrolysis is 25~35° C., the stirring speed is 100~700 rpm, and the pH of the enzymatic hydrolysis is 6.5~8.5.

19. The method for preparing the low molecular weight chondroitin sulfate according to claim 14, wherein protein is removed from hydrolysate by mixed solvents after enzymolysis reaction in a reaction, in which the volume ratio of hydrolysate to mixed solvents is 2~5:1, and the volume ratio of dichloromethane and isopropyl alcohol in the mixed solvents is 3~5:1; and wherein the reaction is stirred at 100~500 rpm for 10~40 min, centrifuged at 3000~5000 rpm for 10~30 min, and the top layer of the reaction solution is taken.

20. The method for preparing the low molecular weight chondroitin sulfate according to claim 19, wherein the upper reaction solution is filtered and sterilized through a 0.22 μm capsule filter after removing the protein, and then the reaction solution is added into 8~12 times volume of anhydrous ethanol for precipitation and dried in vacuum.

21. The method for preparing the low molecular weight chondroitin sulfate according to claim 14, wherein the protein is removed from hydrolysate after enzymolysis reaction by ultrafiltration to obtain reaction solution.

22. The method for preparing the low molecular weight chondroitin sulfate of according to claim 21, wherein the reaction solution is filtered and sterilized through a 0.22 μm capsule filter after removing the protein and then dried in spray.

* * * * *